(12) United States Patent
Roman Gutierrez et al.

(10) Patent No.: US 11,949,203 B2
(45) Date of Patent: Apr. 2, 2024

(54) GAS MANAGEMENT SYSTEM

(71) Applicant: Cymer, LLC, San Diego, CA (US)

(72) Inventors: Yzzer Roman Gutierrez, Escondido, CA (US); Walter Dale Gillespie, Poway, CA (US); Edward Siqi Luo, San Diego, CA (US); Dinesh Adinath Kanawade, San Diego, CA (US)

(73) Assignee: Cymer, LLC, San Diego, CA (US)

( * ) Notice: Subject to any disclaimer, the term of this patent is extended or adjusted under 35 U.S.C. 154(b) by 887 days.

(21) Appl. No.: 16/965,461

(22) PCT Filed: Jan. 10, 2019

(86) PCT No.: PCT/US2019/012999
§ 371 (c)(1),
(2) Date: Jul. 28, 2020

(87) PCT Pub. No.: WO2019/160627
PCT Pub. Date: Aug. 22, 2019

(65) Prior Publication Data
US 2020/0358241 A1 Nov. 12, 2020

Related U.S. Application Data

(60) Provisional application No. 62/630,932, filed on Feb. 15, 2018.

(51) Int. Cl.
*H01S 3/00* (2006.01)
*B01D 53/04* (2006.01)
(Continued)

(52) U.S. Cl.
CPC .............. *H01S 3/036* (2013.01); *B01D 53/04* (2013.01); *B01D 53/30* (2013.01); *B01F 23/191* (2022.01);
(Continued)

(58) Field of Classification Search
CPC ........ H01S 3/036; H01S 3/225; H01S 3/2366; B01D 53/04; B01D 5/30; B01D 2256/18;
(Continued)

(56) References Cited

U.S. PATENT DOCUMENTS 5,978,406 A * 11/1999 Rokni ................. G03F 7/70575
372/59
6,707,529 B1 3/2004 Aoki et al.
(Continued)

FOREIGN PATENT DOCUMENTS

CN 101075095 A 11/2007
CN 102096329 A 6/2011
(Continued)

OTHER PUBLICATIONS

Commissioner, Korean International Searching Authority, International Search Report and Written Opinion, PCT Application No. PCT/US2018/018289, dated Nov. 15, 2018, 23 pages total.
(Continued)

*Primary Examiner* — Anshu Bhatia
(74) *Attorney, Agent, or Firm* — DiBerardino McGovern IP Group LLC

(57) ABSTRACT

A gas chamber supply system includes a gas source configured to fluidly connect to a gas chamber and to supply a gas mixture to the gas chamber, the gas source including: a pre-prepared gas supply including a gas mixture, the gas mixture including a plurality of gas components and lacking a halogen; a recycled gas supply including the gas mixture; and a fluid flow switch connected to the pre-prepared gas supply and to the recycled gas supply. The gas chamber supply also includes a control system configured to: determine if the relative concentration between the gas components within the recycled gas supply is within an acceptable range; and provide a signal to the fluid flow switch to
(Continued)

thereby select one of the pre-prepared gas supply and the recycled gas supply to as the gas source based on the determination.

20 Claims, 11 Drawing Sheets

(51) Int. Cl.
  *B01D 53/30* (2006.01)
  *B01F 23/10* (2022.01)
  *B01F 35/21* (2022.01)
  *B01F 35/221* (2022.01)
  *G01N 33/00* (2006.01)
  *H01S 3/036* (2006.01)
  *H01S 3/225* (2006.01)

(52) U.S. Cl.
  CPC ...... *B01F 35/2132* (2022.01); *B01F 35/2211* (2022.01); *G01N 33/0004* (2013.01); *H01S 3/225* (2013.01); *B01D 2253/104* (2013.01); *B01D 2256/18* (2013.01); *B01D 2257/102* (2013.01); *B01D 2257/104* (2013.01); *B01D 2257/204* (2013.01); *B01D 2257/2066* (2013.01); *B01D 2257/504* (2013.01); *B01D 2257/553* (2013.01); *B01D 2257/80* (2013.01)

(58) Field of Classification Search
  CPC ...... B01D 2257/204; B01D 2257/2066; B01D 2257/504; B01D 2257/80; B01F 35/2132; G01N 33/0004
  See application file for complete search history.

(56) References Cited

U.S. PATENT DOCUMENTS

| | | | |
|---|---|---|---|
| 8,929,419 | B1 | 1/2015 | Dean et al. |
| 9,634,455 | B1 | 4/2017 | Aggarwal |
| 9,819,136 | B2 | 11/2017 | Ahlawat et al. |
| 9,831,627 | B2 | 11/2017 | Vininski et al. |
| 2001/0055101 | A1 | 12/2001 | Hayashi |
| 2006/0285091 | A1 | 12/2006 | Parekh et al. |
| 2007/0268469 | A1 | 11/2007 | Fu et al. |
| 2008/0205472 | A1 | 8/2008 | Dunstan et al. |
| 2011/0128516 | A1 | 6/2011 | Kaneko et al. |
| 2015/0323875 | A1 | 11/2015 | De Graaf et al. |
| 2016/0248215 | A1* | 8/2016 | Suzuki .................. H01S 3/104 |
| 2016/0322772 | A1 | 11/2016 | Abe et al. |
| 2017/0063016 | A1* | 3/2017 | Vininski ............... H01S 3/2255 |
| 2018/0191122 | A1 | 7/2018 | Suzuki et al. |
| 2018/0354795 | A1 | 12/2018 | Suzuki et al. |

FOREIGN PATENT DOCUMENTS

| | | |
|---|---|---|
| CN | 205828871 | 12/2016 |
| CN | 108367923 A | 8/2018 |
| EP | 1843387 A1 | 10/2007 |
| JP | H0429386 A | 1/1992 |
| JP | H1154851 A | 2/1999 |
| JP | H11274662 A | 10/1999 |
| JP | 2000124534 A | 4/2000 |
| JP | 2001232134 A | 8/2001 |
| JP | 6224859 B1 | 11/2017 |
| JP | 2018079461 A | 5/2018 |
| KR | 20180050212 A | 5/2018 |
| TW | 201202869 A | 1/2012 |
| TW | 201714373 A | 4/2017 |
| TW | 201728529 A | 8/2017 |

OTHER PUBLICATIONS

Shane Thomas, United States International Searching Authority, International Search Report and Written Opinion, corresponding PCT Application No. PCT/US2019/012999, dated Mar. 26, 2019, 9 pages total.
Kanawade et al., "Advances in DUV Lightsource Sustainability," Poster No. 10147-72, SPIE Adv. Lithography Conference, San Jose, CA (2017).
Roman et al., "Advances in DUV light source sustainability," Proc. of SPIE, vol. 10147, Optical Microlithography XXX (2017), doi: 10.1117/12.2260307.
"Advanced Lithography Technical Program," SPIE Adv. Lithography Conference, San Jose, CA (2017).
Yashiro et al., "Excimer laser gas usage reduction technology for semiconductor manufacturing," Proc. of SPIE, vol. 10147, Optical Microlithography XXX, doi: 10.1117/12,2257972.
Office Action, counterpart Chinese Patent Application No. 201980013680.1, dated May 22, 2023, 19 pages total (including English translation of 9 pages).
Office Action, Taiwanese Patent Application No. 108103307, dated Dec. 9, 2020, 26 pages total (including English translation of 10 pages).
Office Action and Search Report, counterpart Chinese Patent Application No. 201980013680.1, dated Nov. 2, 2022, 23 pages total (including English translation of 11 pages).
Office Action, Japanese Patent Application No. 2020-540502, dated Oct. 22, 2021, 13 pages total (including English translation of 7 pages).

* cited by examiner

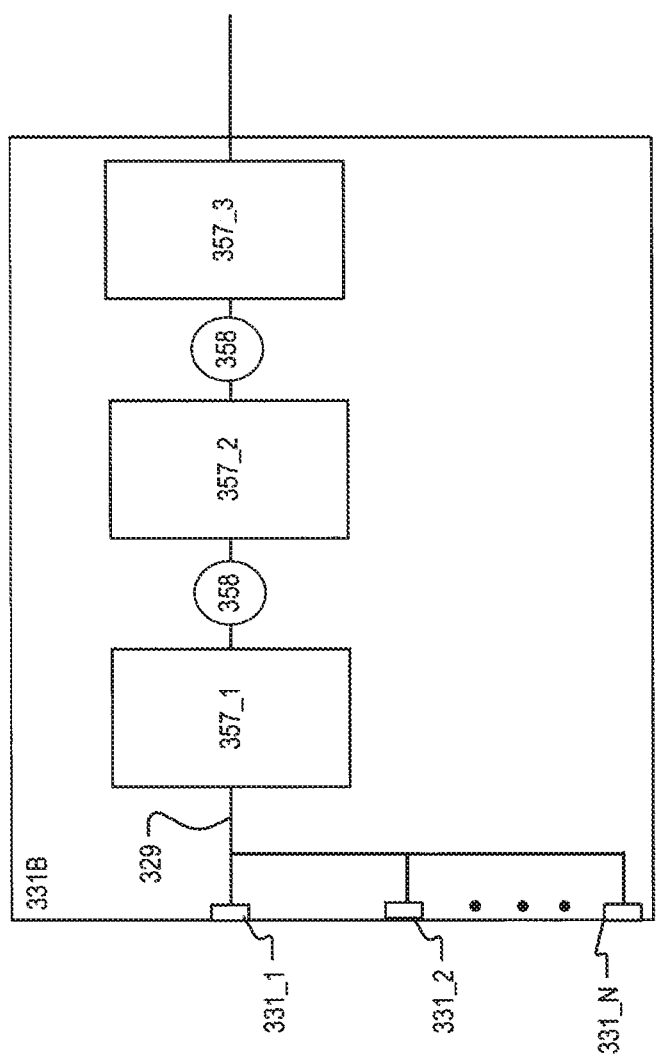

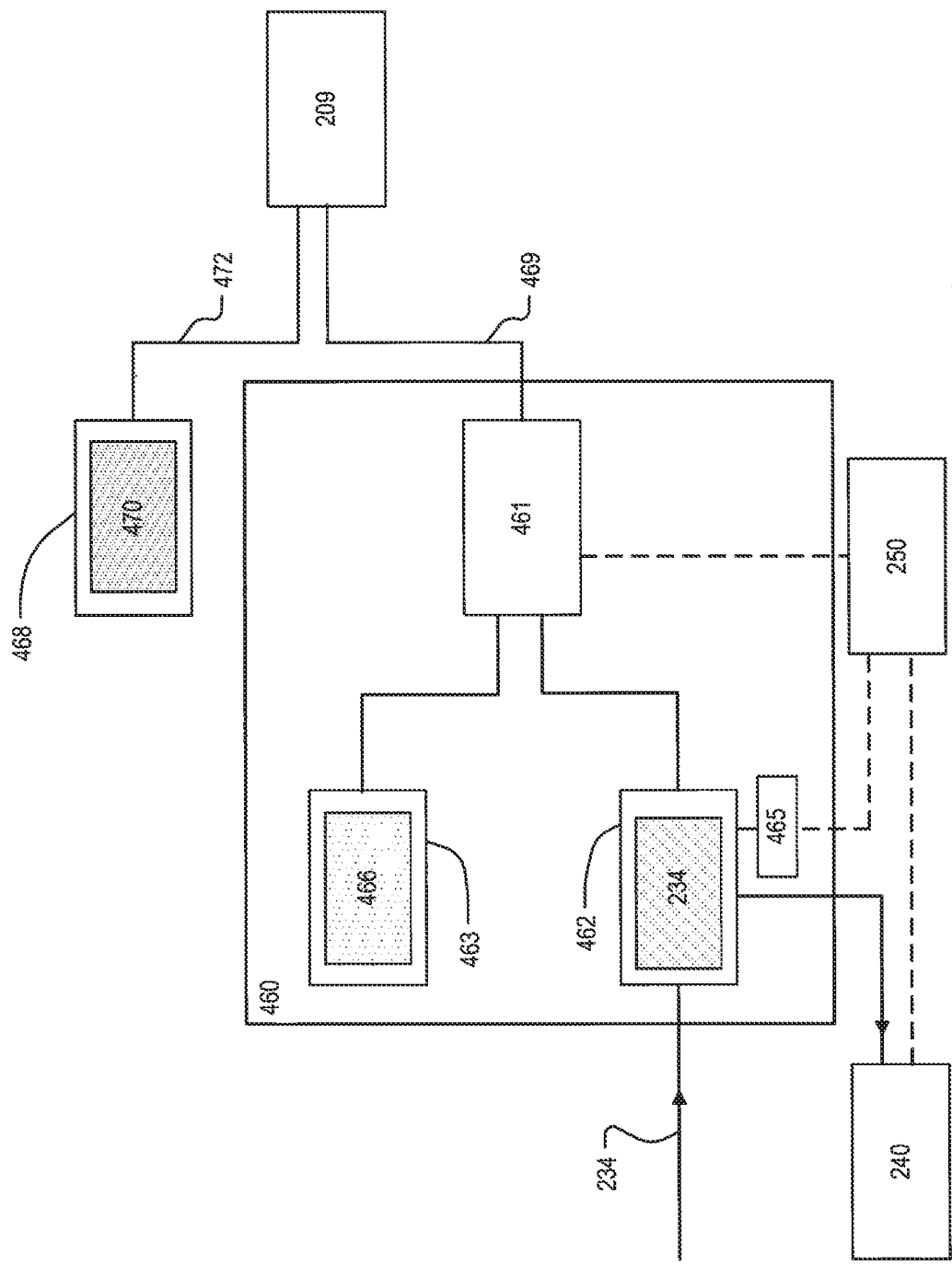

GAS MANAGEMENT SYSTEM

CROSS REFERENCE TO RELATED APPLICATION

This application claims priority of U.S. Provisional Patent Application No. 62/630,932, filed on Feb. 15, 2018, which is incorporated herein in its entirety by reference.

TECHNICAL FIELD

This disclosure relates to a gas management system. The gas management system may be or include a gas recycle system. The gas management system may be used with, for example, a deep ultraviolet light (DUV) source.

BACKGROUND

Photolithography is the process by which semiconductor circuitry is patterned on a substrate such as a silicon wafer. A photolithography optical source provides the deep ultraviolet (DUV) light used to expose a photoresist on the wafer. One type of gas discharge light source used in photolithography is known as an excimer light source or laser. An excimer light source typically uses a gas mixture that is a combination of one or more noble gases, such as argon, krypton, or xenon, and a reactive such as fluorine or chlorine. The excimer light source derives its name from the fact that under the appropriate condition of electrical stimulation (energy supplied) and high pressure (of the gas mixture), a pseudo-molecule called an excimer is created, which only exists in an energized state and gives rise to amplified light in the ultraviolet range. An excimer light source produces a light beam that has a wavelength in the deep ultraviolet (DUV) range and this light beam is used to pattern semiconductor substrates (or wafers) in a photolithography apparatus. The excimer light source can be built using a single gas discharge chamber or using a plurality of gas discharge chambers. The gas mixture in the gas discharge chamber may be exhausted from the gas discharge chamber or chambers.

SUMMARY

In one general aspect, a gas recycle system includes a gas purifier system configured to receive an exhaust gas mixture from an excimer laser, the exhaust gas mixture including intended gas components and impurity gas components, the gas purifier system being configured to reduce an amount of at least one of the impurity gas components to form a purified gas mixture based on the exhausted gas mixture; a gas analysis system including a measurement system configured to receive at least a portion of the purified gas mixture and to measure an amount of at least one intended gas component in the purified gas mixture and an amount of at least one impurity gas component in the purified gas mixture; a gas blending system that prepares a recycled gas mixture based on the purified gas mixture; and a control system coupled to the gas analysis system and the gas blending system, the control system configured to: determine whether the measured amount of the at least one intended gas component is within a first range of acceptable values; determine whether the measured amount of the at least one impurity gas component is within a second range of acceptable values; if the measured amount of the at least one intended gas component is not within the first range of acceptable values, cause the gas blending system to add an additional gas component to the purified gas mixture to prepare the recycled gas mixture; and if the measured amount of the at least one impurity gas is not within the second range of acceptable values, generating an error signal.

Implementations may include one or more of the following features. The impurity gas components may be water ($H_2O$), carbon dioxide ($CO_2$), tetrafluoromethane ($CF_4$), and/or nitrogen trifluoride ($NF_3$). The intended gas components may include at least two noble gases, and the impurity gas components may include any gas that is not a noble gas.

The control system may be configured to generate a command signal that, when provided to a fluid control switch that is connected to a pre-prepared gas mixture and to the recycled gas mixture, causes the fluid control switch to supply the pre-prepared gas mixture to a laser and to not supply the recycled gas mixture to the laser.

Each of the impurity gas components may be associated with a respective range of acceptable values, and the control system may be configured to determine whether the measured amount of each impurity gas component is within the acceptable range of values for that impurity gas component.

The measurement system may be a mass spectrometer, a gas chromatograph, or a Fourier-transform infrared (FTIR) spectrometer.

The control system may be configured to add a noble gas to the purified gas mixture. The purified gas mixture may include at least some of the noble gas prior to the control system causing the gas blending system to add the noble gas to the purified gas mixture.

In another general implementation, a gas recycle system includes a gas blending system that receives a purified gas mixture and prepares a recycled gas mixture based on the received purified gas mixture; a gas analysis system including a measurement system configured to: measure an amount of at least one noble gas in the purified gas mixture received at the gas blending system, and measure an amount of the at least one noble gas in the prepared recycled gas mixture; and a control system configured to: determine whether the measured amount of the at least one noble gas in the purified gas mixture received at the gas blending system is within an acceptable range of values; if the measured amount of the at least one noble gas in the purified gas mixture is not within the range of acceptable values, cause the gas blending system to add at least one additional gas component to the purified gas mixture to prepare the recycled gas mixture; and determine whether the measured amount of the at least one noble gas in the prepared recycled gas mixture is within the acceptable range of values.

Implementations may include one or more of the following features. The control system may be further configured to cause a gas supply system to provide the prepared recycled gas to an excimer laser only if the measured amount of the at least one noble gas in the prepared recycled gas mixture is within the acceptable range of values.

The purified gas mixture may include at least two noble gases, the measurement system may be configured to measure an amount of each of the at least two noble gases in the purified gas mixture received at the gas blending system, the measurement system may be configured to measure an amount of each of the at least two noble gases in the prepared recycled gas mixture, each of the two or more noble gases may be associated with an acceptable range of values, and the control system may be configured to determine whether the measured amount of each noble gas in the purified gas mixture and in the prepared recycled gas mixture is within the acceptable range of values for that noble gas.

The measurement system may be a mass spectrometer, a gas chromatograph, or a Fourier-transform infrared (FTIR) spectrometer.

In another general aspect, a gas recycle system includes a laser exhaust gas collection system including a plurality of inlet ports and an outlet port, each inlet port being configured to be fluidly coupled to an exhaust gas outlet port of an excimer laser; a gas purifier system fluidly coupled to the outlet port of the laser exhaust gas collection system and configured to produce a purified gas mixture based on gas mixtures exhausted from any of the excimer lasers fluidly coupled to the laser exhaust gas collection system; a gas analysis system including a measurement system configured to measure an amount of at least one gas component in the purified gas mixture; a gas blending system that prepares a recycled gas mixture based on the purified gas mixture; and a control system coupled to the gas analysis system and the gas blending system, the control system configured to: determine whether the measured amount of the at least one gas component is within a range of acceptable values; and if the measured amount of the at least one gas component is not within the range of acceptable values, causing the gas blending system to add an additional gas component to the purified gas mixture to prepare the recycled gas mixture.

Implementations may include one or more of the following features. The gas analysis system may be further configured to measure an amount of the at least one gas component in the recycled gas mixture. The control system may be further configured to determine whether the measured amount of the at least one gas component in the recycled gas mixture is within the acceptable range of values. The at least one gas component of the purified gas mixture may include a noble gas.

The at least one gas component of the purified gas mixture may include two or more noble gases and a plurality of impurity gas components, the measurement system may be configured to measure an amount of all of the gas components in the purified gas mixture, and the control system may be configured to determine whether the measured amount of each of the gas components is within an acceptable range of values for that gas component.

The impurity gas components may include water ($H_2O$), carbon dioxide ($CO_2$), tetrafluoromethane ($CF_4$), and/or nitrogen trifluoride ($NF_3$).

In some implementations, the gas recycle system also includes a gas supply system configured to receive the prepared recycled gas and to provide the prepared recycled gas to one or more excimer lasers. The prepared recycled gas may be provided to one or more excimer lasers that are different from the excimer lasers coupled to laser exhaust gas collection system.

In another general aspect, a gas chamber supply system includes a first gas source configured to fluidly connect to a first inlet of a first gas chamber and configured to supply a first gas mixture that contains a first plurality of gases, at least one of the gases in the first plurality includes a halogen. The gas chamber supply system also includes a second gas source configured to fluidly connect to a second inlet of the first gas chamber and configured to supply a second gas mixture that contains a second plurality of gases, the second plurality of gases lacking a halogen, the second gas source including: a pre-prepared gas supply including the second gas mixture; a recycled gas supply including the second gas mixture; and a fluid flow switch connected to the pre-prepared gas supply and to the recycled gas supply. The gas chamber supply system also includes a gas analysis system that receives a sample of the recycled gas supply and analyzes gas components within the recycled gas supply; and a control system connected to the gas analysis system and to the fluid flow switch and configured to: receive the analysis from the gas analysis system; determine if the relative concentration between the gas components within the recycled gas supply is within an acceptable range; and provide a signal to the fluid flow switch to thereby select one of the pre-prepared gas supply and the recycled gas supply as the second gas source based on the determination.

Implementations may include one or more of the following features. The gas chamber supply system also may include a pressure measurement system configured to measure a pressure of the recycled gas supply. The control system may receive an output from the pressure measurement system, and may adjust the signal to the fluid flow switch based on the output from the pressure measurement system.

The second gas mixture may include at least a gain medium component having a noble gas and at least a buffer component. The noble gas in the gain medium component may be Ar and the buffer component may include a noble gas. The analysis of the gas components within the recycled gas supply may include measuring an amount of the gain medium component having the noble gas and measuring an amount of the buffer component.

The recycled gas supply including the gas mixture may be received from a gas blending system of a gas recycle system.

The gas analysis system may be a mass spectrometer, a gas chromatograph, or a Fourier-transform infrared (FTIR) spectrometer.

In another general aspect, a gas chamber supply system includes a first gas source configured to fluidly connect to a first inlet of a first gas chamber and configured to supply a first gas mixture that contains a first plurality of gases, at least one of the gases in the first plurality includes a halogen; and a second gas source configured to fluidly connect to a second inlet of the first gas chamber and configured to supply a second gas mixture that contains a second plurality of gases, the second plurality of gases lacking a halogen. The second gas source includes a pre-prepared gas supply including the second gas mixture; a recycled gas supply including the second gas mixture; and a fluid flow switch connected to the pre-prepared gas supply and to the recycled gas supply. The gas chamber supply system also includes a gas recycle system configured to supply the second gas mixture to the recycled gas supply. The gas recycle system includes a gas purifier system configured to receive a gas mixture exhausted from a second gas chamber that is distinct from the first gas chamber; a gas analysis system that receives the purified gas mixture and analyzes the gas components within the purified gas mixture; and a gas blending system that prepares a recycled gas mixture and outputs the recycled gas mixture as the second gas mixture of the recycled gas supply. The gas chamber supply system also includes a control system connected to the gas recycle system and to the fluid flow switch, and configured to provide a signal to the fluid flow switch to thereby select one of the pre-prepared gas supply and the recycled gas supply as the second gas source.

Implementations may include one or more of the following features. The gas chamber supply system also may include a pressure measurement system configured to measure a pressure of the recycled gas supply. The control system may receive an output from the pressure measurement system, and may adjust the signal to the fluid flow switch based on the output from the pressure measurement system.

The purified gas mixture may include at least a gain medium component having a noble gas and at least a buffer component. The noble gas in the gain medium component may be Ar and the buffer component may include a noble gas.

The analysis of the gas components within the purified gas mixture may include measuring an amount of the gain medium component having the noble gas and measuring an amount of the buffer component.

The gas analysis system may include a mass spectrometer, a gas chromatograph, or a Fourier-transform infrared (FTIR) spectrometer.

In another general aspect, a gas chamber supply system includes a first gas source configured to fluidly connect to a first inlet of a first set of gas chambers, and configured to supply a first gas mixture that contains a first plurality of gases, at least one of the gases in the first plurality includes a halogen; and a second gas source configured to fluidly connect to a second inlet of the first set of gas chambers, and configured to supply a second gas mixture that contains a second plurality of gases, the second plurality of gases lacking a halogen. The second gas source includes a pre-prepared gas supply including the second gas mixture; a recycled gas supply including the second gas mixture; and a fluid flow switch connected to the pre-prepared gas supply and to the recycled gas supply. The gas chamber supply system also includes a gas recycle system configured to supply the second gas mixture to the recycled gas supply, the gas recycle system including: a gas purifier system fluidly connected to the output to receive a gas mixture exhausted from at least one of the gas chambers of a second set of gas chambers; a gas analysis system that receives the purified gas mixture and analyzes the gas components within the purified gas mixture; and a gas blending system that prepares a recycled gas mixture and outputs the recycled gas mixture as the second gas mixture of the recycled gas supply. The gas chamber supply also includes a control system connected to the gas recycle system and to the fluid flow switch, and configured to provide a signal to the fluid flow switch to thereby select one of the pre-prepared gas supply and the recycled gas supply as the second gas source.

Implementations may include one or more of the following features. One or more of the gas chambers of the second set may correspond to one or more of the gas chambers of the first set.

The gas chamber supply system also may include a pressure measurement system configured to measure a pressure of the recycled gas supply. The control system may receive an output from the pressure measurement system, and may adjust the signal to the fluid flow switch based on the output from the pressure measurement system.

The purified gas mixture may include at least a gain medium component having a noble gas and at least a buffer component. The noble gas in the gain medium component may be Ar and the buffer component may include a noble gas.

The analysis of the gas components within the purified gas mixture may include measuring an amount of the gain medium component having the noble gas and measuring an amount of the buffer component.

The gas analysis system may include a mass spectrometer, a gas chromatograph, or a Fourier-transform infrared (FTIR) spectrometer.

Implementations of any of the techniques described above and herein may include a process, an apparatus, and/or a method. The details of one or more implementations are set forth in the accompanying drawings and the description below. Other features will be apparent from the description and drawings, and from the claims.

BRIEF DESCRIPTION OF THE DRAWINGS

FIG. 3B is a block diagram of an example of an exhaust gas collection system.

FIG. 4 is a block diagram of an example of a gas supply system.

DETAILED DESCRIPTION

Figure 1:
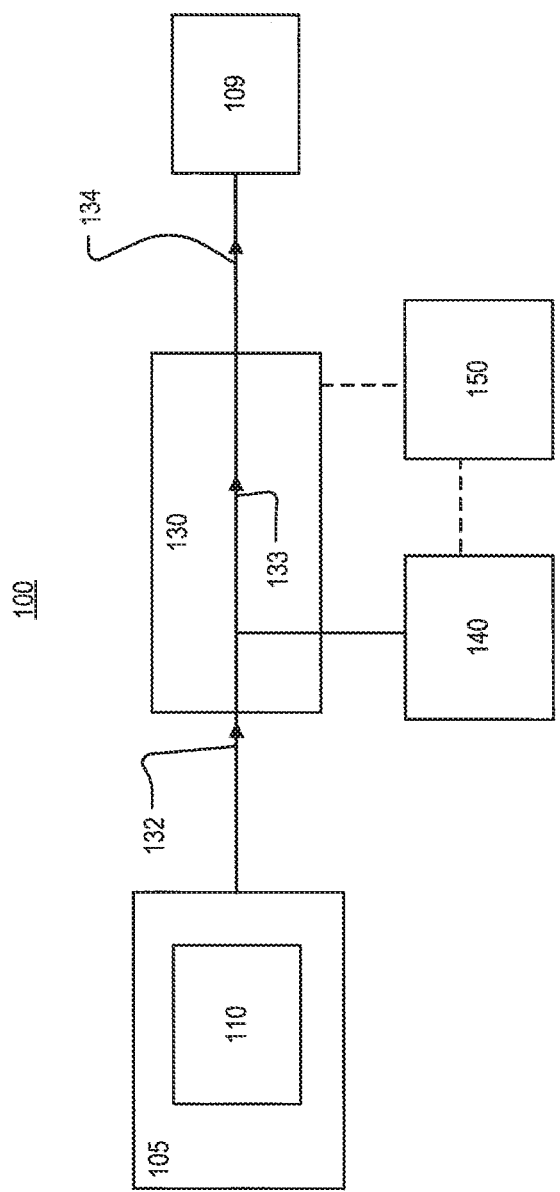
FIG. 1 is a block diagram of an example of a gas management system.

Referring to FIG. 1, a block diagram of a gas management system 100 is shown. The gas management system 100 includes a gas recycle system 130 and a gas analysis system 140. The gas recycle system 130 receives an exhaust gas mixture 132 from a discharge chamber 110 of an optical source 105 and produces a recycled gas mixture 134. The gas analysis system 140 analyzes a gas mixture 133 that flows in the gas recycle system 130. In the examples shown in FIGS. 1-5, a dashed lines between elements represents a wired and/or wireless communication path through which data and information are exchanged. A solid line illustrates a path through which a fluid such as a gas flows.

Figure 9:
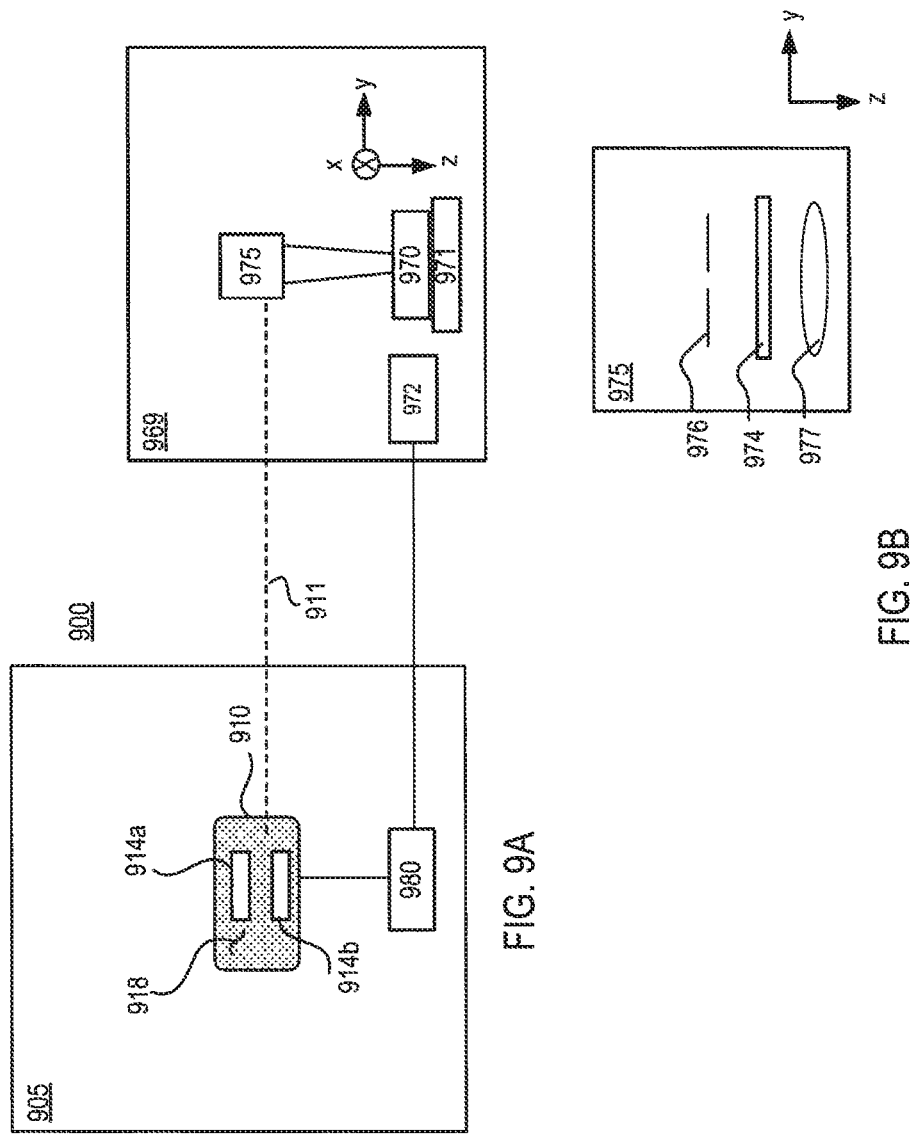
FIG. 9A is a block diagram of an example of a photolithography system.
FIG. 9B is a block diagram of an example of a projection optical system that may be used in, for example, the photolithography system of FIG. 9A.
Figure 10:
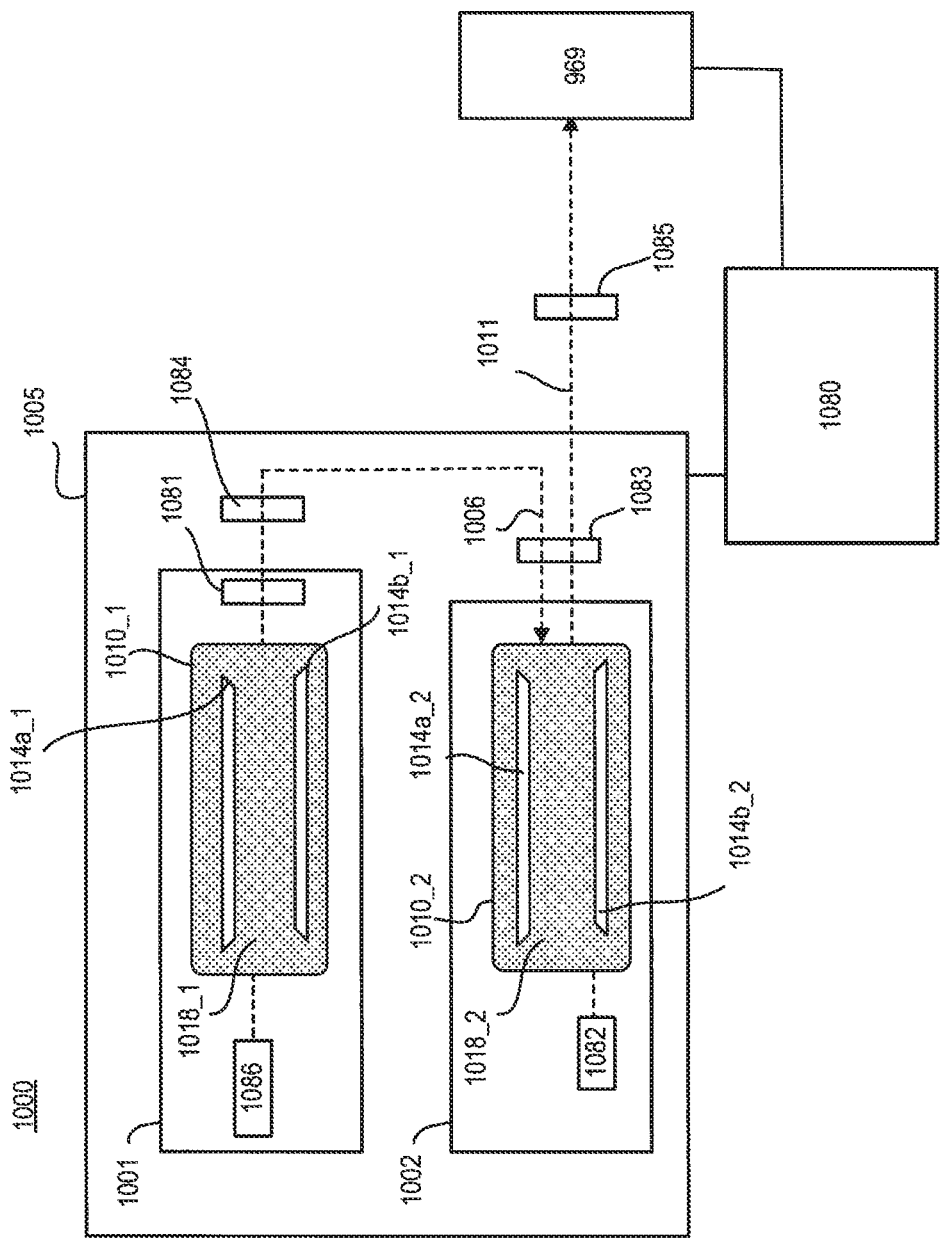
FIG. 10 is a block diagram of another example of a photolithography system.

The recycled gas mixture 134 is supplied to a chamber 109. The chamber 109 may be the discharge chamber 110 of the optical source 105, another discharge chamber of the optical source 105, a discharge chamber of one or more other optical sources, and/or a supply tank that holds the recycled gas mixture 134 for possible later use. The optical source 105 is any optical source that includes a discharge chamber that uses a gaseous gain medium. For example, the optical source 105 may be an excimer laser. The optical source 105 may be a deep ultraviolet (DUV) optical source, such as shown in FIGS. 9A and 10. The optical source may be used as part of a DUV lithography system, such as shown in FIG. 9B.

As discussed below, the gas recycle system 130 implements a multi-stage recycling process to produce the recycled gas mixture 134. The gas mixture 133 may be a gas mixture at any stage in the recycling process. For example, the gas mixture 133 may be the exhaust gas mixture 132, a purified gas mixture formed by the gas recycle system 130, and/or the recycled gas mixture 134. Thus, the gas analysis system 140 measures the components of the gas mixture 133 at any or all of the stages in the gas recycle system 130.

A gas mixture (such as the exhaust gas mixture 132, the recycled gas mixture 134, or the gas mixture 133) is a material made up of two or more different components or substances (such as gases) that are mixed but are not combined chemically. For example, the exhaust gas mixture 132 is a physical combination of two or more gases in which the identities of the gases are retained and are mixed. The components of a gas mixture may be pure gases, for example, gases that are made up of individual atoms of one element (for example, a noble gas), elemental molecules that are made from one type of atom (for example, oxygen gas), or compound molecules that are made from a variety of atoms (for example, carbon dioxide or water).

The gas analysis system 140 directly measures the amount of the various components of the gas mixture 133, including impurity components. A control system 150 is coupled to the gas recycle system 130 and the gas analysis system 140. The control system 150 compares the measured amounts to a known specification to access the usability of the recycled gas mixture 134. If the measured amounts are outside of the specification, the control system 150 generates a command signal that causes the gas recycle system 130 to add a gas component to the gas mixture 133 to produce the recycled gas mixture 134.

The gas recycle system 130 may reduce costs of a system that uses the optical source 105. The recycled gas mixture 134 is based on the exhaust gas mixture 132. Thus, the gas recycle system 130 allows one or more gases to be reused, leading to cost savings and conservation of natural resources. Moreover, the gas recycle system 130 may lead to improved performance. For example, some prior systems estimate the make-up of the gas mixture in the discharge chamber 110 indirectly by measuring an optical property (such as a beam quality) of an optical beam produced by the optical source 105. On the other hand, the gas recycle system 130 uses a direct measurement of the gas mixture 133. By measuring the components of the gas mixture 133 directly, the recycled gas mixture 134 produced by the gas recycle system 130 may be corrected to be within a specification that is common to an entire class or type of optical source instead of just a particular monitored optical source. As such, the recycled gas mixture 134 may be provided to an optical source other than the optical source 105.

Furthermore, the gas recycle system 130 analyzes the gas mixture 133 for impurity components, and, in some implementations, the gas management system 100 prevents recycled gas that has an unacceptable level of impurity components from being supplied to an optical system. Using a gas mixture that includes an unacceptably high amount of impurity components in the discharge chamber of an optical source may degrade the performance of that optical source. Thus, as compared to a recycle system that does not analyze impurity components, the gas recycle system 130 improves performance of the optical system or optical systems that are configured to receive the recycled gas mixture 134.

Figure 2:
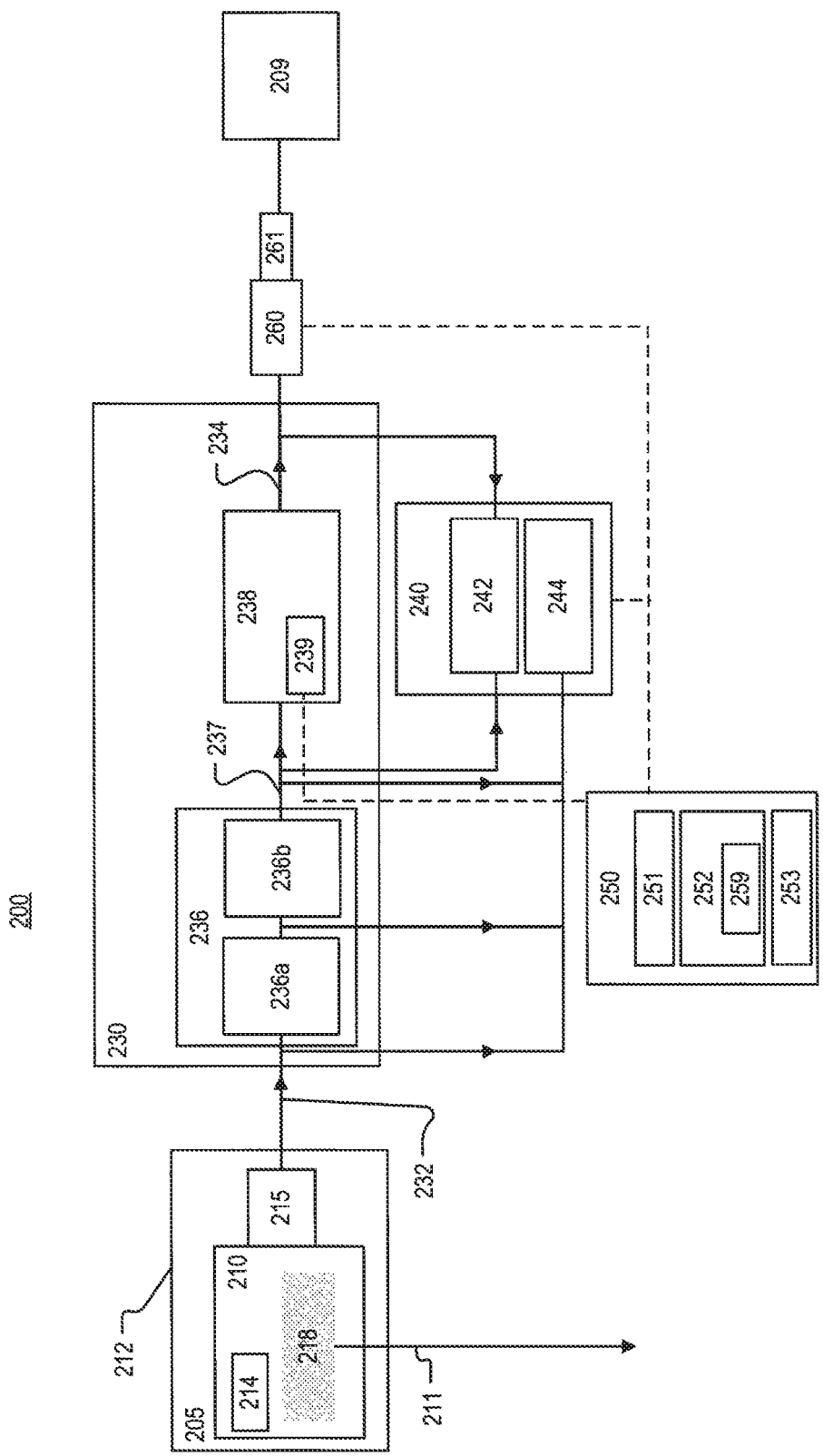
FIG. 2 is a block diagram of another example of a gas management system.

Referring to FIG. 2, a block diagram of a gas management system 200, which includes a gas recycle system 230, is shown. The gas recycle system 230 is an example of an implementation of the gas recycle system 130 (FIG. 1). The gas recycle system 230 receives an exhaust gas mixture 232 from a discharge chamber 210 of an optical source 205.

The discharge chamber 210 includes an energy source 214 and a gas mixture 218 inside of a housing 212. The gas mixture 218 includes a gain medium formed from one or more noble gases and a halogen gas. For example, the noble gas of the gain medium may be Krypton (Kr), Argon (Ar), and/or Xenon (Xe), and the halogen gas may be fluorine (F). The gas mixture 218 also includes a buffer gas that does not react with the halogen gas. Thus, the buffer gas may be a noble gas such as, for example, Neon (Ne) or Helium (He). The energy source 214 provides energy to the gas mixture 218 sufficient to cause a population inversion in the gain medium and to enable generation of an output light beam 211 via stimulated emission. For example, the energy source 214 produces an electric field in the discharge chamber 210. The generated electric field accelerates the electrons in the gain medium, and the electrons collide with neutral atoms (such as the buffer gas) in the gas mixture 218. The collisions cause electrons in the lower energy state of the gain medium to jump to a higher energy state, and a population inversion occurs in the gain medium such that an output light beam 211 is generated through stimulated emission.

The gases that make up the gain medium and the buffer gas are referred to as intended gases or intended gas components because these gases are present for the production of the output light beam 211. The gas mixture 218 also may include other gas components that are not intentionally or purposefully placed in the discharge chamber. These other gas components are referred to as impurity gas components. The impurity gas components may include, for example, impurities and byproducts formed as a result of applying energy to the gas mixture 218. The impurity gas components may include, for example, oxygen ($O_2$), water ($H_2O$), carbon dioxide ($CO_2$), tetrafluoromethane ($CF_4$), and/or nitrogen trifluoride ($NF_3$). The impurity components may be inorganic or organic.

Over the lifetime of an optical source that uses a gaseous gain medium (such as the optical source 205), the gas mixture 218 may be replaced completely in a replacement operation or it may be replaced partially in an injection operation. To reduce consumption of natural resources (such as Ne and He), and to reduce costs, the gas mixture 218 is recycled using the gas recycle system 230. The gas recycle system 230 receives the exhaust gas mixture 232 and produces a recycled gas mixture 234 from the exhaust gas mixture 232, and this recycled gas mixture 234 is supplied to a chamber 209. As discussed above, the chamber 209 may be the discharge chamber 210 of the optical source 205, another discharge chamber of the optical source 205, a discharge chamber of one or more other optical sources, and/or a supply tank that holds the recycled gas mixture 234 for later use by a chamber. Additionally, the gas recycle system 230 removes or reduces the impurity components in the exhaust gas mixture 232 and directly measures the amount of remaining impurity components to ensure that recycled gas mixture 234 that is supplied to the chamber 209 lacks the impurity gas components or has impurity gas components in acceptable amounts.

The gas mixture 218 in the discharge chamber 210 interacts with a scrubber 215 prior to being exhausted from the optical source 205. The scrubber 215 captures the halogen gas in the gas mixture 218 such that the halogen gas is not exhausted out of the discharge chamber 210 and is not part of the exhaust gas mixture 232. The scrubber 215 is part of the optical source 205. The scrubber 215 is an enclosed volume that uses, for example, activated alumina to scrubber or remove the halogen gas (for example, fluorine) from the exhaust gas mixture 232 so that the halogen gas does not enter the gas recycle system 232.

The gas recycle system 230 includes a gas purification system 236 that receives the exhaust gas mixture 232. The gas purification system 236 removes some or all of the impurity components from the exhaust gas mixture 232 to form a purified gas mixture 237. The purified gas mixture 237 is a gas mixture that includes a smaller amount of at least one of the gas components in the exhaust gas mixture 232 or a gas mixture that does not include at least one of the gas components in the exhaust gas mixture 232.

In the example of FIG. 2, the gas purification system 236 includes two purification stages: a regenerative purifier 236a and a getter purifier 236b. The purification stages 236a and 236b are placed in series and are fluidly coupled such that the exhaust gas mixture 232 interacts first with the purification stage 236a and then with the purification stage 236b to form the purified gas mixture 237.

The regenerative purifier 236a is designed to remove reactive gases from the exhaust gas mixture 232. The gases removed by the regenerative purifier 236a may include, for example, oxygen ($O_2$), nitrogen ($N_2$), and/or residual halogen gas not removed by the scrubber 215. The regenerative purifier 236a may have a filtration media that is able to be refreshed or regenerated instead of being replaced. The regenerative purifier 236a may be regenerated by, for example, exposing the filtration media to hydrogen or a mixture of hydrogen and another inert gas. In some implementations, the regenerative purifier 236a may be a purifier produced by Advanced Research Manufacturing (ARM) of Colorado Springs, Colorado. Although the purification stage 236a of FIG. 2 is a regenerative purifier, other purifiers may be used. For example, the purification stage 236a may be a purifier that is not regenerative but is still able to remove reactive gases from the exhaust gas mixture 232.

The getter purifier 236b is designed to remove non-reactive impurity compounds, such as, for example, carbon dioxide ($CO_2$), carbon monoxide (CO), nitrogen trifluoride ($NF_3$), tetrafluorosilane ($SiF_4$) and tetrafluoromethane ($CF_4$). The getter purifier 236b may remove gaseous impurities using adsorption.

The gas recycle system 230 also includes a gas blending system 238, which receives the purified gas mixture 237. The gas blending system 238 forms the recycled gas mixture 234 from the purified gas mixture 237. The gas blending system 238 includes a gas storage system 239, which includes one or more tanks, each of which store a gas that may be added to the purified gas mixture 237. The gas blending system 238 only adds gas to the purified gas mixture 237 when the components of the purified gas mixture 237 are not within specification. Thus, when the components of the purified gas mixture 237 meet the specification, the purified gas mixture 237 becomes the recycled gas mixture 234.

The gas recycle system 230 includes a gas analysis system 240 that measures an amount of one or more components in the purified gas mixture 237. A control system 250 commands the gas blending system 238 based on the measured amount or amounts from the gas analysis system 240. The gas analysis system 240 includes a measurement system 242, which interacts with a portion of the purified gas mixture 237 to determine an amount of one or more components of the purified gas mixture 237. For example, the measurement system 242 may receive a sample of the purified gas mixture 237 and determine the amounts of one or more components in the purified gas mixture 237 based on the sample. Additionally, the measurement system 242 may sample the recycled gas produced by the gas blending system 238 to measure amounts of various gas components in the recycled gas mixture 234.

The measurement system 242 may be any device that is capable of making a direct measurement of the components of the purified gas mixture 237. In some implementations, the measurement system 242 is any device that is capable of measuring the amount of more than one components of the purified gas mixture 237. For example, the measurement system 242 is a mass spectrometer, a gas chromatograph, or a Fourier-transform infrared (FTIR) spectrometer. A mass spectrometer ionizes a sampled gas mixture and sorts the ions based on their mass-to-charge ratio. A gas chromatograph separates and analyzes compounds that are able to be vaporized without decomposition. An FTIR spectrometer obtains an infrared spectrum of an absorption or an emission of a gas. The various components of the gas are identified from the obtained infrared spectrum. Other apparatuses may be used as the measurement system 242. For example, the measurement system 242 may be an apparatus based on discharge or laser-induced breakdown emission spectroscopy, a cavity ring-down spectrometer, or an apparatus based on chemical or electro-chemical sensing.

Regardless of the apparatus used for the measurement system 242, the measurement system 242 receives a portion of the purified gas mixture 237 and measures an amount of one or more components in the purified gas mixture 237. Additionally, the measurement system 242 may measure the gas components in the recycled gas mixture 234 produced by the gas blending system 238.

In some implementations, the gas analysis system 240 also includes a sensor system 244. The sensor system 244 includes one or more sensors that measure a single, specific component in a gas mixture. For example, the sensor system 244 may include an oxygen sensor. In these implementations, the sensor system obtains a sample of the exhaust gas mixture 232 (before the exhaust gas mixture 232 interacts with the gas purification system 236) and measures an amount of oxygen in the exhaust gas mixture 232. The sensor system 244 may include more than one of the same type of sensor such that a particular gas component may be measured at more than one point in the gas recycle system 230. For example, the sensor system 244 may include an additional oxygen sensor that samples the exhaust gas mixture 232 after interacting with the regenerative purifier 236a but before interacting with the getter purifier 236b. The gas component or components that are measured with the sensor system 244 may also be measured by the measurement system 242.

The control system 250 is coupled to the gas analysis system 240 and the gas blending system 238. The control system 250 includes an electronic processor 251, an electronic storage 252, and an I/O interface 253. The electronic processor 251 includes one or more processors suitable for the execution of a computer program such as a general or special purpose microprocessor, and any one or more processors of any kind of digital computer. Generally, an electronic processor receives instructions and data from a read-only memory, a random access memory, or both. The electronic processor 251 may be any type of electronic processor.

The electronic storage 252 may be volatile memory, such as RAM, or non-volatile memory. In some implementations, and the electronic storage 252 includes non-volatile and volatile portions or components. The electronic storage 252 may store data and information that is used in the operation of the control system 250, components of the control system 250, and/or systems controlled by the control system 250. The information may be stored in, for example, a look-up table or a database. For example, the electronic storage 252 may store data that defines a specification for the recycled gas mixture 234. The specification may indicate a range of acceptable values for each of a plurality of gas components. The range of acceptable values may be expressed as a range of relative values, such as a range of acceptable concentration percentages for each gas component and/or as a range of absolute measurement values, such as a minimum and maximum concentration of each gas component in parts-per-million (ppm).

Moreover, the electronic storage 252 may store various recipes or process programs 259 that dictate actions of the gas blending system 238 and/or analyze data from the gas analysis system 240. The process programs 259 may be implemented as digital logic and/or instructions that when executed by the processor 251 cause various components of the gas analysis system 240 and/or the gas recycle system 230 to perform an action specified by the instructions. The process programs 259 may include a recipe that indicates that when measurement data from the gas analysis system 240 indicates that an amount of a gas component is outside of the acceptable range of values, gas from a particular one of the tanks in the gas storage system 239 is added to the purified gas mixture 237 by opening a valve (not shown) that allows the gas in that tank to flow into the purified gas mixture 237. In another example, the electronic storage 252 may store a recipe that indicates values of parameters that define how the gas blending system 238 adds gas from the gas storage system 239 to the purified gas mixture 237. For example, such a recipe may include values such as a temporal duration for opening a valve that allows gas from the gas storage system 239 to enter the purified gas mixture 237 to thus control an amount of gas added to the purified gas mixture 237. In yet another example, the recipe may include information that relates to a mass flow controller that measures and/or controls the flow of the gas from the storage system 239 into the purified gas mixture 237. In still another example, the process programs 259 may include instructions that cause the control system 250 to generate various error signals when one or more of the gas components in the purified gas mixture 237 is outside of a range of acceptable amounts. For example, the control system 250 may cause the I/O interface 253 to produce a perceivable warning that displays a visual warning on a screen, produces an audible alarm, and/or produces a visual alarm other than a display on a screen, such as causing a light indicator to emit light. In some implementations, the control system 250 may cause an alert to be sent to an operator via text message or email. In yet another example, the process programs 259 may include a process program that accesses data received from the gas analysis system 240 and determines relative amounts of a plurality of gas components in the gas sampled by the gas analysis system 240.

In addition to the process programs 259, the electronic storage 252 also may store instructions, perhaps as a computer program, that, when executed, cause the processor 251 to communicate and exchange data with components in the control system 250, the optical source 205, the gas recycle system 230, a separate and external computer system or systems, and/or the chamber 209. For example, the processor 251 may communicate command signals to the control system 250, the optical source 205, and/or the gas recycle system 230 that are sufficient to activate and/or deactivate devices within these elements. For example, the processor 251 may communicate command signals to the gas recycle system 230 that causes valves in the gas recycle system 230 to open or close.

The I/O interface 253 is any kind of electronic interface that allows the control system 250 to receive and/or provide data and signals with an operator, the optical source 205, the gas recycling system 230, the measurement system 242, and/or an automated process running on another electronic device. For example, the I/O interface 253 may include one or more of a visual display, a keyboard, and a communications interface.

The gas management system 200 also includes a gas supply system 260, which is fluidly connected to the gas blending system 238 and stores the recycled gas mixture 234. The gas supply system 260 is also connected to the control system 250. The control system 250 may provide commands to the gas supply system 260 to control whether and/or how the recycled gas mixture 234 is released from the gas recycle system 230 to the chamber 209. For example, the control system 250 may control a valve 261 to open only when the recycled gas mixture 234 does not include any impurity components that are outside of an acceptable range of values. In some implementations, the control system 250 determines that the recycled gas mixture 234 does not meet a specification or requirement (for example, by having impurity components that are outside of the acceptable range of values) and the control system 250 causes the recycled gas mixture 234 to be exhausted someplace other than the chamber 209, such as, for example, an exhaust port.

Figure 3A:
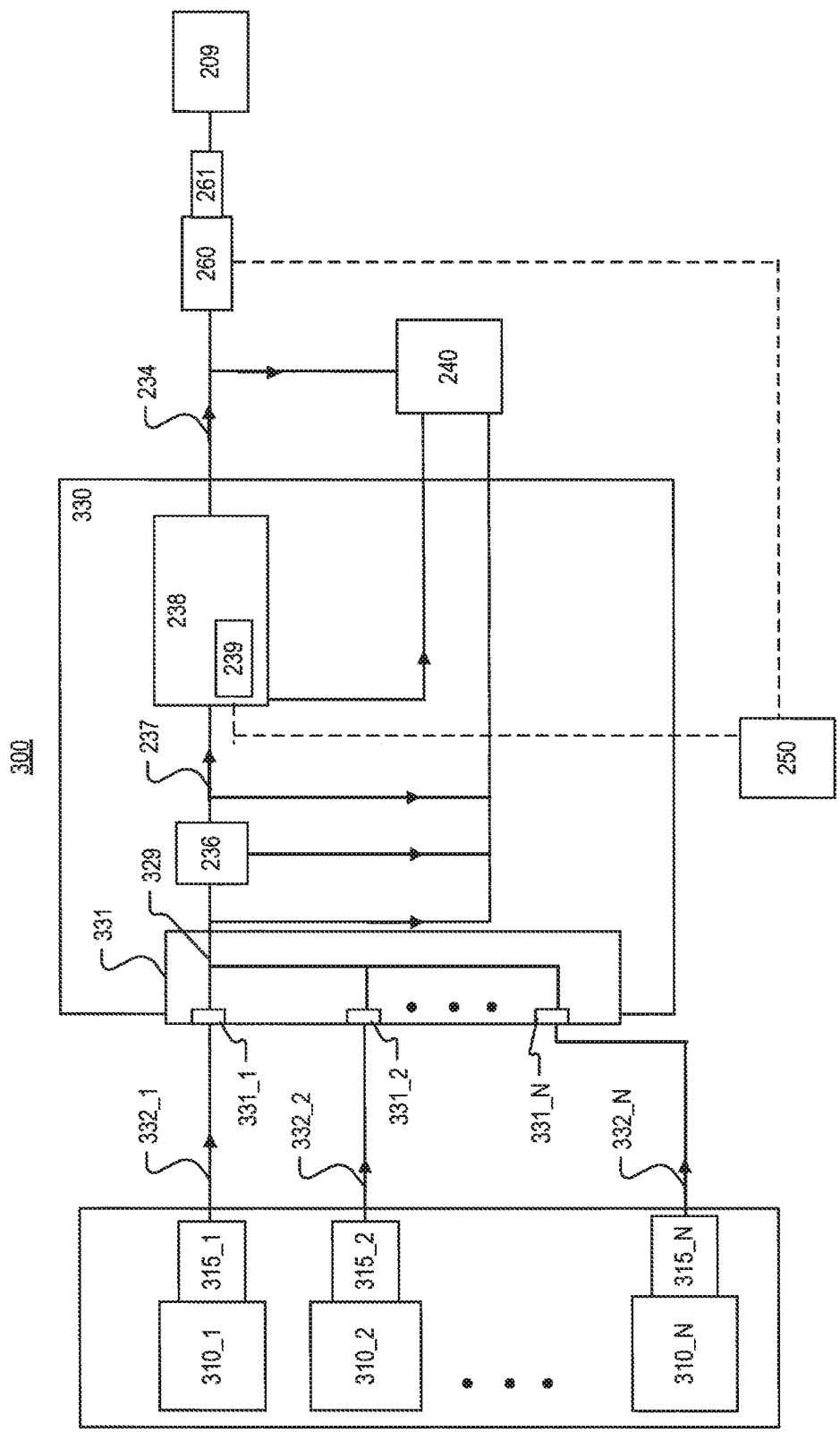
FIG. 3A is a block diagram of another example of a gas management system.

Referring to FIG. 3A, a block diagram of a gas management system 300, which includes a gas recycle system 330, is shown. The gas recycle system 330 is another example implementation of the gas recycle system 130 (FIG. 1). The gas recycle system 330 is similar to the gas recycle system 230 (FIG. 2), except the gas recycle system 330 includes an exhaust gas collection system 331. The exhaust gas collection system 331 allows the gas recycle system 330 to receive an exhaust gas mixture from more than one optical source.

The exhaust gas collection system 331 includes N inlets 313_1 to 331_N, where N is an integer number greater than one. For example, N may be equal to five. Each of the N inlets 331_1 to 331_N is configured to be fluidly connected to a respective discharge chamber 310_1 to 310_N and to receive an exhaust gas mixture 332_1 to 332_N. Each discharge chamber 310_1 to 310_N may be an instance of the discharge chamber 210 (FIG. 2) and includes the gas mixture 218 and a respective scrubber 315_1 to 315_N. Each of the inlets 331_1 to 331_N is fluidly connected to a fluid bus 329 that is fluidly coupled to the gas purification system 236. The fluid bus 329 is any structure that is capable of transporting fluid (for example, a gas mixture) from more than one source or container. For example, the fluid bus 329 may be a pipe or conduit that defines a region through which fluid may flow. The pipe or conduit also includes fittings or junctions where more than one pipe or conduit are fluidly sealed together and form a larger open space through which fluid may flow. The pipe or conduit also includes valves that are configured to isolate portions of the pipe or conduit. In this way, the fluid bus 329 enables any or all of the exhaust gas mixtures 332_1 to 332_N to flow into the purifier 236.

At any given time, the exhaust gas collection system 331 receives an exhaust gas mixture from any or all of the connected discharge chambers 310_1 to 310_N. A discharge chamber exhausts substantially all of the gas mixture 218 during a refill operation, but only a portion of the gas mixture 218 during an injection operation. For example, the volume of gas exhausted from a discharge chamber during a refill operation may be more than 100 liters (L). The volume of gas exhausted from a discharge chamber during an inject operation may be as low as about 1 L. The exhaust gas collection system 331 has a capacity to receive an exhaust gas mixture from all of the discharge chambers 310_1 to 310_N during simultaneous inject operations. In some implementations, the exhaust gas collection system 331 is configured to receive 3 to 40 liters per second. Furthermore, the exhaust gas collection system 331 has a capacity sufficient to process over 90% of the exhaust gas mixture from all of the discharge chambers 310_1 to 310_N during simultaneous gas event operations.

Referring also to FIG. 3B, a block diagram of an exhaust gas collection system 331B is shown. The exhaust gas collection system 331B is an example of an implementation of the exhaust gas collection system 331 (FIG. 3A). The exhaust gas collection system 331B includes one or more storage tanks. In the example shown in FIG. 3B, the collection system 331B includes three storage tanks 357_1, 357_2, 357_3. The tank 357_1 is fluidly coupled to the fluid bus 329 and the inlets 331_1 to 331_N. The tank 357_1 is maintained at a negative pressure by a pump 358 to avoid backpressure. Negative pressure means that the gas recycler system 230 is constantly pulling any flow of exhausted gas, so as to not create back pressure that could interfere with the normal operation of the optical source 205. The tanks 357_2 and 357_3 collect the exhaust gas that flows into any of the inlets 331_1 to 331_N. The arrangement of the exhaust gas collection system 331B produces a steady gas flow to the purifier system 236. The steady gas flow allows the purifier system 236 to operate efficiently.

Referring to FIG. 4, a block diagram of a gas supply system 460 is shown. The gas supply system 460 is an example of an implementation of the gas supply system 260 (FIGS. 2 and 3A). The gas supply system 460 is discussed with respect to the gas recycle system 230. However, the gas supply system 460 may be used with other gas recycle systems, such as the gas recycle system 130 or 330.

Figure 5:
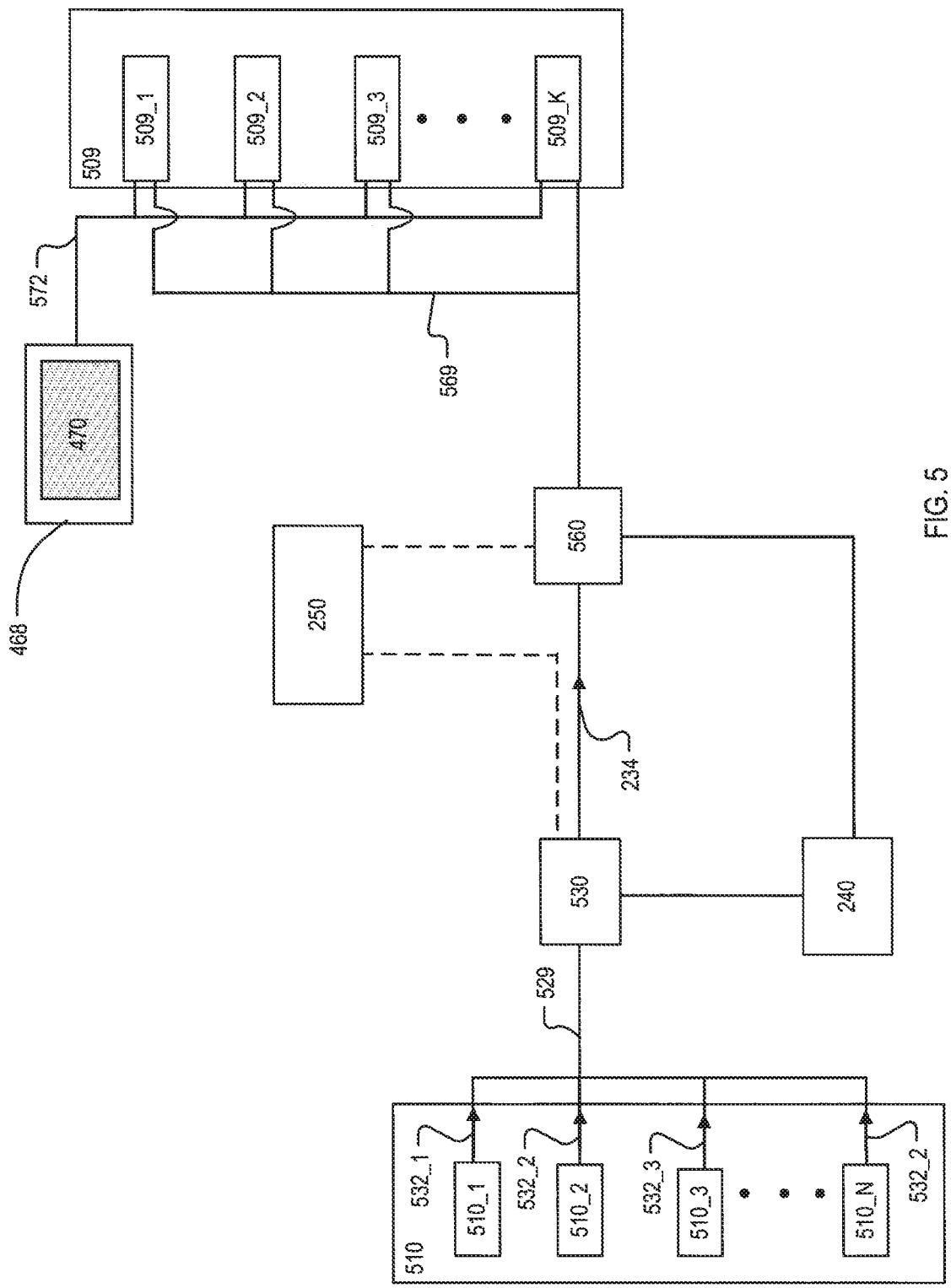
FIG. 5 is a block diagram of another example of a gas management system.

The gas supply system 460 includes a fluid switch 461 that allows selection between the recycled gas mixture 234 and a pre-prepared or pre-prepared gas mixture 466. The gas supply system 460 is fluidly coupled to the chamber 209 through a fluid bus 469. The fluid switch 461 ensures, for example, that the chamber 209 (which may be a discharge chamber of a single optical source or a collection of discharge chambers such as shown in FIG. 5) only receives the recycled gas mixture 234 when the recycled gas mixture 234 is within specifications.

The gas supply system 460 also includes a tank system 462, which receives the recycled gas mixture 234 produced by the gas blending system 238 (FIG. 2). The tank system 462 includes one or more tanks, chambers, or other structures that hold the recycled gas mixture 234. The gas analysis system 240 samples the recycled gas mixture 234 and measures the amounts of the various components in the recycled gas mixture 234. In the example of FIG. 4, the gas analysis system 240 is in fluid communication with at least one tank of the tank system 462 such that a sample of the recycled gas mixture 234 may be received at the measurement system 242 and the components measured. In the implementation shown in FIG. 4, the tank system 462 is part of the gas supply system 460. In other implementations, the tank system 462 is external to the gas supply system 460 but is still fluidly coupled to the switch 461.

The gas supply system 460 also includes a tank system 463. The tank system 463 includes one or more tanks, chambers, or other structures that are able to contain fluids. The tank system 463 holds the pre-prepared gas mixture 466. The pre-prepared gas mixture 466 may be a bi-mix that includes two primary gas components (the gain medium noble gas and a buffer gas that is also a noble gas) and no impurities, or trace amounts of impurities that are within the specifications of the chamber 209. The bi-mix lacks a halogen gas. For example, the pre-prepared gas mixture 466 may be a mixture of Ar and another gas such as Ne, with each of these gases present in the pre-prepared gas mixture 466 in amounts that are within specifications for the chamber 209.

The pre-prepared gas mixture 466 is not prepared or otherwise generated by the gas recycling system 230. In other words, the pre-prepared gas mixture 466 does not interact with the gas purification system 236 (FIG. 2) or the gas blending system 238 (FIG. 2). Instead, the pre-prepared gas mixture 466 is generated by a separate process and supplied pre-mixed in final form in a tank that is incorporated into the gas supply system 460. For example, the tank system 463 may be incorporated into the gas supply system 460 by an operator of the gas recycle system 230. The pre-prepared gas mixture 466 includes intended gas components and impurity gas components that are within the specifications of the discharge chamber 209. The pre-prepared gas mixture 466 in the tank system 463 does not include a halogen gas.

The tank system 462 and the tank system 463 are fluidly coupled to the fluid switch 461. The fluid switch 461 may include, for example, two valves, one of which controls the flow of the pre-prepared gas mixture 466 from the tank system 463 and the other of which controls the flow of the recycled gas mixture 434 from the tank system 462. The fluid switch 461 may be configured to allow only one of the recycled gas mixture 434 or the pre-prepared gas mixture 466 to flow through the switch 461 to the fluid bus 469. Thus, when used with the fluid switch 461, the tank system 462 and the tank system 463 are alternative sources of gas mixtures or alternative supply sources for the chamber 209.

The control system 250 compares the measured amounts of the various components in the recycled gas mixture 234 to the specification to determine whether the recycled gas mixture 234 is acceptable for use in the chamber 209. If the recycled gas mixture 234 is acceptable for use in the chamber 209, the control system 250 provides a signal to the fluid switch 461 that is sufficient to cause the fluid switch 461 to select the tank system 462 as the supply source. For example, the signal may be sufficient to cause the valve coupled to the tank system 462 to open and the valve coupled to the tank system 463 to close so that only the recycled gas mixture 234 flows through the fluid switch 461 to the fluid bus 269. If the recycled gas mixture 234 is not acceptable for use in the chamber 209, the control system 250 provides a signal to the fluid switch that causes the fluid switch 461 to select the tank system 463 as the supply source.

In some implementations, the tank system 462 is coupled to a pressure monitoring system 465 that monitors the pressure of the recycled gas mixture 434 that is held in the tank system 462 and provides an indication of the pressure of the recycled gas mixture 434. In these implementations, the control system 250 also may use the indication of the pressure to determine which of the tank systems 462 and 463 to select as the supply source. For example, a measured pressure that is below a threshold indicates that the amount of the recycled gas mixture 234 in the tank system 462 is insufficient to supply the chamber 209. When the measured pressure is below the threshold amount, the control system 250 may provide a signal to the fluid switch to select the tank system 463 regardless of the composition of the recycled gas mixture 234.

Thus, either the recycled gas mixture 234 or the pre-prepared gas mixture 466 flows through the fluid switch 461 and to the fluid bus 469. As discussed above, neither the recycled gas mixture 234 nor the pre-prepared gas mixture 466 includes a halogen gas. However, a halogen gas is typically one of the intended gas components in a gas mixture used in the chamber 209. To supply a halogen gas to the chamber 209, a gas mixture 470 from a second supply system 468 flows through a separate conduit 472 that is fluidly coupled to the chamber 209 and the second supply system 468. The second supply system 468 contains a gas mixture 470 that includes a halogen gas. The gas mixture 470 is a tri-mix, which is a mixture of the gain medium noble gas, a buffer gas (which is also a noble gas), and a halogen (that is a part of the gain medium). For example, the gas mixture 470 may be a mixture of Ar, Ne, and F. The gas mixture 470 may flow in the fluid bus 472 and be supplied to the chamber 209.

Referring to FIG. 5, a block diagram of a gas management system, which includes a gas recycle system 530, is shown. The gas recycle system 530 may be any of the gas recycle systems 130, 230, or 330 discussed above. The gas recycle system 530 is fluidly coupled to a chamber system 510. The chamber system 510 includes N discrete gas discharge chambers 510_1 to 510_N, where N is an integer number greater than one. Each of the discharge chambers 510_1 to 510_N is part of an optical source that uses a gaseous gain medium (such as the optical source 205 of FIG. 2), and each of the discharge chambers 510_1 to 510_N releases a respective exhaust gas mixture 532_1 to 532_N during a refill or injection operation. The discharge chambers 510_1 to 510_N are fluidly coupled to a fluid bus 529, which flows into the gas recycle system 530. The gas recycle system 530 produces the recycled gas mixture 234 based on the exhaust gas mixture or mixtures 532_1 to 532_N that flow into the gas recycle system 530.

The recycled gas mixture 234 is stored at a gas supply system 560 and may be provided to one or more discharge chambers in a discharge chamber system 509. The discharge chamber system 509 includes discharge chambers 509_1 to 509_K, where K is an integer number greater than one. Although K and N may be the same number, that is not necessarily the case. Thus, the number of discharge chambers supplied by the gas recycle system 530 may be greater than, less than, or equal to the number of discharge chambers from which an exhaust gas mixture is received. Moreover the discharge chamber system 509 may include some or all of the discharge chambers 510_1 to 510_N, or the all of the discharge chambers 509_1 to 509_K may be separate and independent from the discharge chambers 510_1 to 510_N.

The gas supply system 560 may be fluidly coupled to the discharge chamber system 509 via a fluid bus 569. The gas supply system 560 may be the gas supply system 460 such that the recycled gas mixture 234 is only provided to the discharge chamber system 509 when the fluid switch 461 permits the recycled gas mixture 234 to flow to the fluid bus 569. A separate fluid bus 572 fluidly couples the second supply system 468, which holds the halogen-containing gas mixture 470, and the discharge chamber system 509. The halogen-containing gas mixture 470 is supplied to the discharge chamber system 509 via the separate fluid bus 572.

Figure 6:
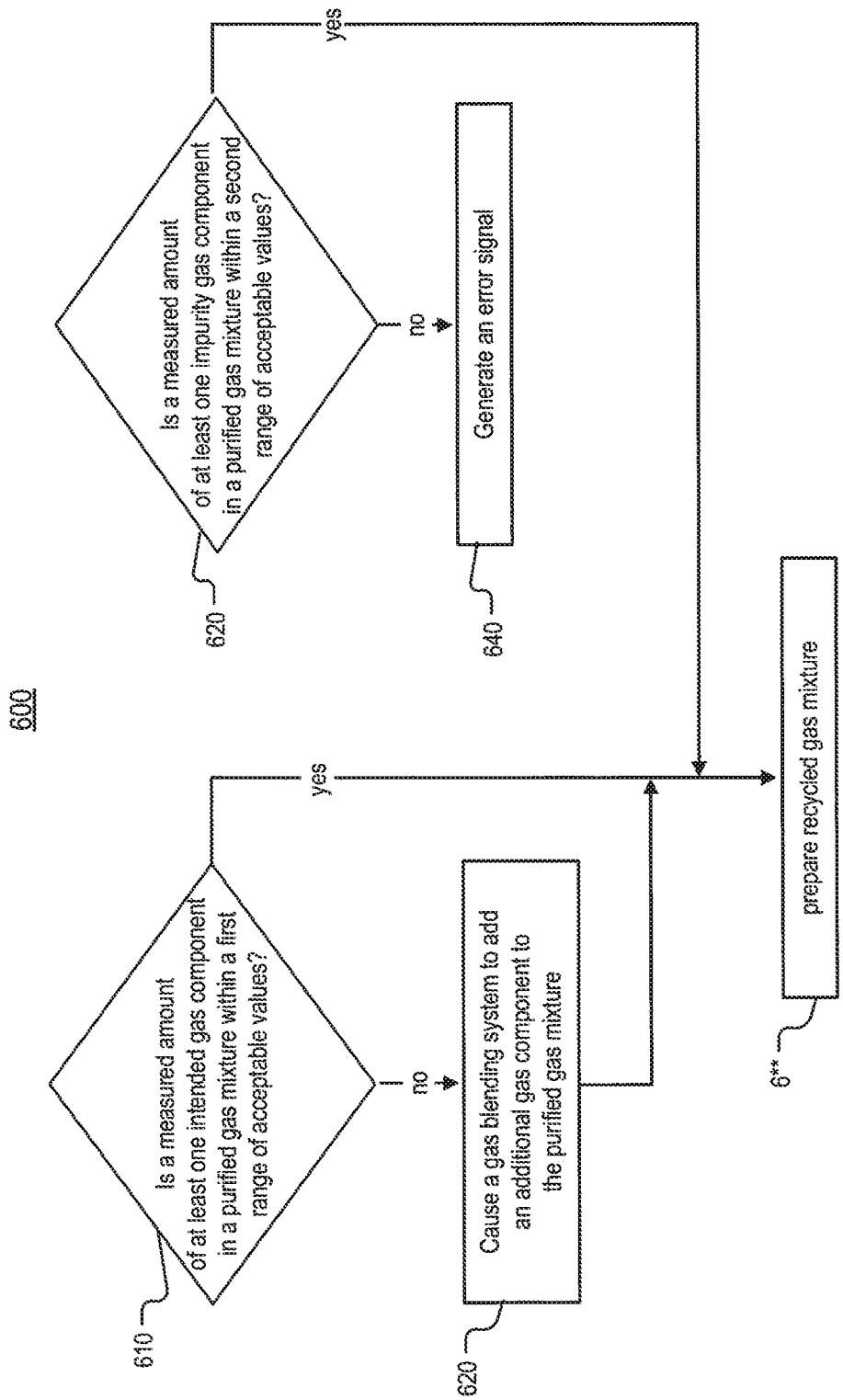
FIG. 6 is a flow chart of an example of a process for managing gas components in a recycled gas mixture.

FIG. 6 is a flow chart of an example of a process 600 for managing gas components in a recycled gas mixture. FIG. 6 may be performed by the one or more processors 251 of the control system 250. FIG. 6 is discussed with respect to FIGS. 2 and 4.

The control system 250 determines whether a measured amount of an intended gas component in the purified gas mixture 237 is within a first range of values (610). The intended gas component may be, for example, a noble gas that is used as part of the gain medium of the optical source 205 or as a buffer gas. The intended gas component may be, for example, Ar, Ne, He, and/or Xe. The measured amount of the intended gas component is obtained by the measurement system 242. The control system 250 may access the measurement from the measurement system 242, or the measurement system 242 may provide the measurement to the control system 250. The first range of values is a range of values between which the amount of the intended gas component is acceptable.

The first range of values is part of a specification that defines acceptable values and/or ranges of values for gas components in a gas mixture that is used in the chamber 209. The specification may be stored in the electronic storage 252 in a look-up table or database. The specification may be stored in association with a particular type of optical source such that the same specification is used to evaluate all recycled gas mixtures that may be used in those sources.

The specification may include a specific range of values or a threshold value for each of a plurality of gas components. For example, the specification may include a range of acceptable values for Ar, another range of acceptable values for Ne, and another range of acceptable values for Xe. In some implementations, the control system 250 makes the determination 610 by obtaining measured amounts of more than one intended gas component, and then comparing the measured amounts for each of the measured intended gas components to a respective range of acceptable values. For example, measured intended gas components may include measured amounts of two or more noble gases.

The range of acceptable values may be a range of percentages of that gas component relative to the entire gas mixture, or an absolute measurement. For example, the specification may define the acceptable amount of Ne as 96.4% to 96.6%, the acceptable amount of Ar as 3.4% to 3.6%, and the acceptable amount of Xe as 8 to 10 ppm. Measured values that are inside the ranges defined by the specification are acceptable. Measured values that are outside the ranges defined by the specification are not acceptable.

Additionally, the specification defines acceptable amounts of impurity gas components. The control system 250 determines whether a measured amount of an impurity gas component in the purified gas mixture 237 is within a second range of values (620). The second range of values is a range of values that is associated with the measured impurity. An impurity gas component is any gas component in the purified gas mixture 237 that is not an intended gas component. Oxygen ($O_2$), water ($H_2O$), carbon dioxide ($CO_2$), tetrafluoromethane ($CF_4$), and/or nitrogen trifluoride ($NF_3$) are examples of impurity compounds. The acceptable amount of water may be, for example, less than 0.5 ppm. Thus, the acceptable range of values for water vapor is between zero and 0.5 ppm.

If the measured amount of the at least one intended gas component is not within a first range of acceptable values (610), then the control system 250 commands the gas blending system 238 to add an additional gas component to the purified gas mixture 237 (630). The additional gas component may be an additional amount of an intended gas that is already present in the purified gas. For example, the additional gas component may be a mixture that includes more than one noble gas.

The electronic storage 252 may store recipes that indicate what type of gas component to add to the purified gas mixture 237 based on the measured composition of the purified gas mixture 237. For example, if the purified gas mixture 237 has too little Ar, the recipe may specify that the gas blending system 238 add a gas mixture that includes Ar and Xe to the purified gas mixture 237. In another example, if the purified gas mixture 237 has too little Xe, the recipe may specify that the gas blending system 238 add a gas mixture that includes Ne, Ar, and Xe to the purified gas mixture 237 to prepare the recycled gas mixture 234. If all of the intended gas components in the purified gas mixture 237 are within specification, then the purified gas mixture 237 is used as the recycled gas mixture 234.

As discussed above, impurity gas components are also analyzed at 620. If the measured amount of the at least one impurity gas component in the purified gas mixture 237 is not within the second range of values (620), then the control system 250 generates an error signal (640). For example, the control system 250 may cause the I/O interface 253 to produce a perceivable warning (such as a visual warning that is presented on a screen, an audible sound, and/or a visually perceivable warning that is not displayed on a screen) and/or may cause an alert to be sent to an operator via text message or email. In some implementations, the error signal is provided directly to another portion of the gas management system 200. For example, in implementations that include the gas supply system 460 (FIG. 4), the error signal may command the fluid switch 461 to not allow the recycled gas mixture 234 to flow through the switch 461 such that the pre-prepared gas mixture 466 flows through the switch 461 and the recycled gas mixture 234 is exhausted from the gas recycled system 230.

After the gas blending system 238 adds the additional gas component to the purified gas mixture 237 (630), then the process 600 can proceed to prepare the recycled gas mixture 234 for output by the gas management system 200 (650). Although not shown, it is possible that the control system 250 perform one or more additional steps after commanding the gas blending system 238 to add the additional gas component to the purified gas mixture 237 (630) before the recycled gas mixture 234 is prepared for output to the gas supply system 260 (650). For example, the control system 250 can repeat the determination into whether the measured amount of the intended gas component in the purified gas mixture 237 is within the first range of values (610) and if the measured amount of the intended gas component in the purified gas mixture 237 is within the first range of values (610), then the recycled gas mixture 234 can be prepared for output by the gas management system 200 (650).

Figure 7:
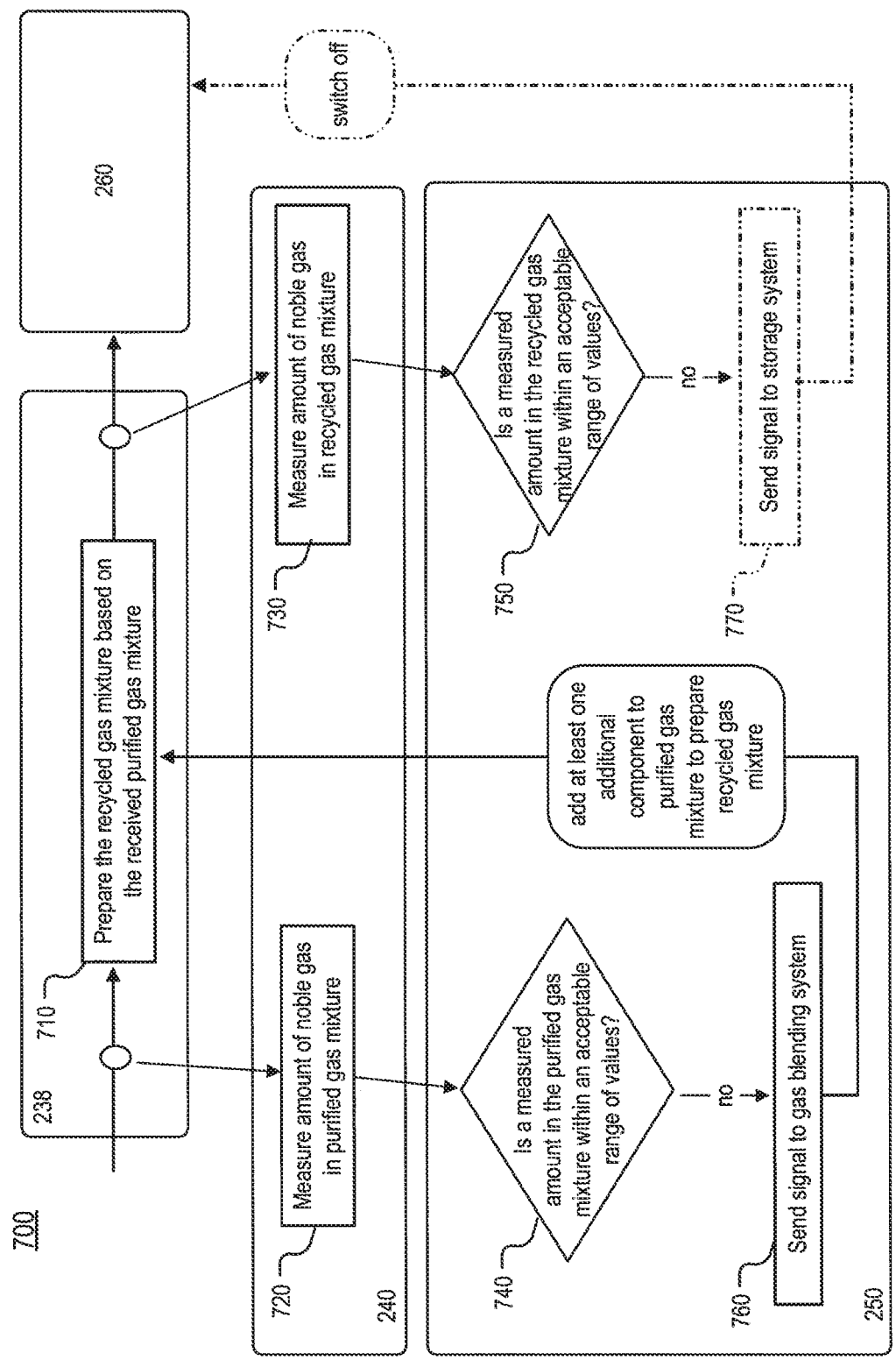
FIG. 7 is a flow chart of an example process performed by a gas management system.

Referring to FIG. 7, a process 700 may be performed by the various components of the gas management system 200. The gas blending system 238 receives the purified gas mixture 237 and prepares the recycled gas mixture 234 based on the received purified gas mixture (710). The gas analysis system 240 (for example, the measurement system 242) receives a sample or portion of the purified gas mixture 237 that is directed to the gas blending system 238 and measures an amount of at least one noble gas in this received purified gas mixture (720). The gas analysis system 240 (for example, the measurement system 242) also receives a sample or portion of the prepared recycled gas mixture from the gas blending system 238, and measures an amount of the at least one noble gas in the prepared recycled gas mixture 234 (730).

The control system 250 (which is in communication with the gas analysis system 240) receives the measured amount of the at least one noble gas in the purified gas mixture (720) and determines whether the measured amount of the at least one noble gas in the purified gas mixture received at the gas blending system 238 is within an acceptable range of values (740). If the measured amount of the at least one noble gas is not within the range of acceptable values (740), then the control system 250 sends a signal to the gas blending system 238 to thereby cause the gas blending system 238 to add at least one additional gas component to the purified gas mixture 237 to prepare the recycled gas mixture 234 (760). The control system 250 also receives the measured amount of the at least one noble gas in the prepared recycled gas mixture 234 (730), and determines whether the measured amount of the at least one noble gas in the prepared recycled gas mixture 234 is within the acceptable range of values (750).

Although not required, the control system 250 may instruct the gas supply system 260 or 460 to switch off the supply of the tank system 462 (which supplies the recycled gas mixture 234) to the chamber 209 (770) if the control system 250 determines that the measured amount of the at least one noble gas in the prepared recycled gas mixture 234 is not within the acceptable range of values (750).

Figure 8:
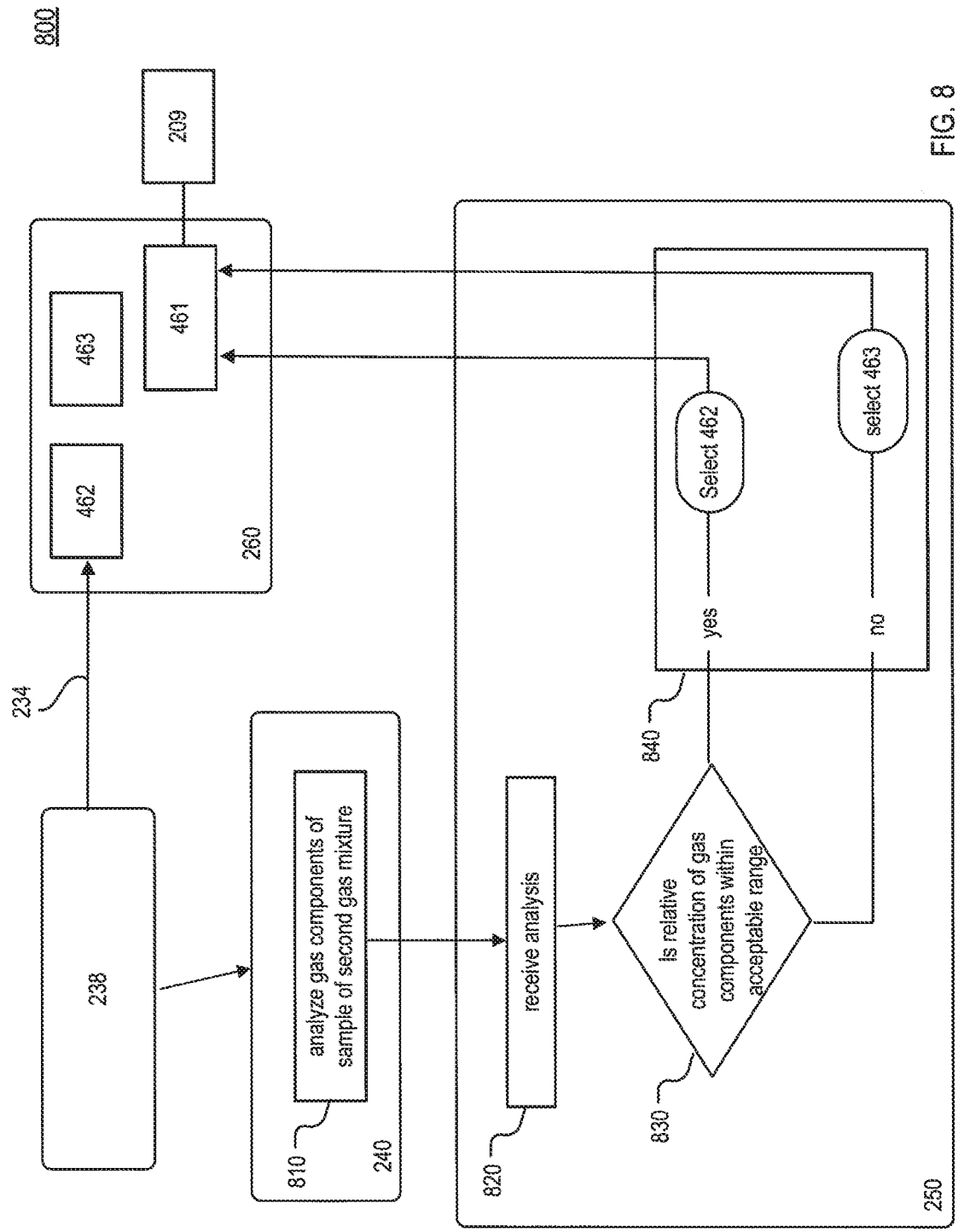
FIG. 8 is a flow chart of an example of a process for switching between a pre-prepared gas mixture and a recycled gas mixture.

Referring to FIG. 8, the gas management system 200 may perform a process 800 to switch between the pre-prepared gas mixture 466 (in the tank system 463) and the recycled gas mixture 234 (in the tank system 462) to supply a suitable bi-mix to the chamber 209 by way of the fluid bus 469. Reference is also made to FIGS. 2 and 4 when discussing the process 800. The gas analysis system 240 receives a sample of the recycled gas mixture 234 from the gas blending system 238, and analyzes the gas components within the recycled gas mixture 234 (810). The control system 250 receives the analysis (810) from the gas analysis system 240 (820). The control system 250 determines if the relative concentration between the gas components within the recycled gas mixture 234 is within an acceptable range (830). The control system 250 provides a signal (840) to the fluid switch 461 to thereby select one of the pre-prepared gas mixture 466 (in the tank system 463) or the recycled gas mixture 234 (in the tank system 462) based on this determination 830. In particular, if the control system 250 determined (830) that the relative concentration of gas components in the recycled gas mixture 234 is not within an acceptable range, then the control system 250 sends a signal to the fluid switch 461 to obtain the bi-mix from the pre-prepared gas mixture 466 in the tank system 463. On the other hand, if the control system 250 determined (830) that the relative concentration of gas components in the recycled gas mixture 234 is within an acceptable range, then the control system 250 sends a signal to the fluid switch 461 to obtain the bi-mix from the recycled gas mixture 234 in the tank system 462.

FIGS. 9A and 10 provide examples of DUV light sources 905 and 1005, respectively, that include discharge chambers that may be supplied with the recycled gas mixture 234 and/or may provide the exhaust gas mixture 232 to the gas management system 200.

Referring to FIGS. 9A and 9B, a photolithography system 900 includes an optical (or light) source 905 that provides a light beam 911 to a lithography exposure apparatus 969, which processes a wafer 970 received by a wafer holder or stage 971. The optical source 905 includes a discharge chamber 910, which encloses a cathode 914a and an anode 914b. Only one gas discharge chamber 910 is shown in FIG. 9A; however, the light source 905 may include more than one discharge chamber.

The light beam 911 is a pulsed light beam that includes pulses of light separated from each other in time. The lithography exposure apparatus 969 includes a projection optical system 975 through which the light beam 911 passes prior to reaching the wafer 970, and a metrology system 972. The metrology system 972 may include, for example, a camera or other device that is able to capture an image of the wafer 970 and/or the light beam 911 at the wafer 970, or an optical detector that is able to capture data that describes characteristics of the light beam 911, such as intensity of the light beam 911 at the wafer 970 in the x-y plane. The lithography exposure apparatus 969 may be a liquid immersion system or a dry system. The photolithography system 900 also includes a control system 980 to control the optical source 905 and/or the lithography exposure apparatus 969.

Microelectronic features are formed on the wafer 970 by, for example, exposing a layer of radiation-sensitive photoresist material on the wafer 970 with the light beam 911. Referring also to FIG. 9B, the projection optical system 975 includes a slit 976, a mask 974, and a projection objective, which includes a lens system 977. The lens system 977 includes one or more optical elements. The light beam 911 enters the optical system 975 and impinges on the slit 976, and at least some of the beam 911 passes through the slit 976. In the example of FIGS. 9A and 9B, the slit 976 is rectangular and shapes the light beam 911 into an elongated rectangular shaped light beam. A pattern is formed on the mask 974, and the pattern determines which portions of the shaped light beam are transmitted by the mask 974 and which are blocked by the mask 974. The design of the pattern is determined by the specific microelectronic circuit design that is to be formed on the wafer 970.

Referring to FIG. 10, a block diagram of a photolithography system 1000 is shown. The system 1000 is an example of an implementation of the system 900 (FIG. 9A). For example, in the photolithography system 1000, an optical source 1005 is used as the optical source 905 (FIG. 9A). The optical source 1005 produces a pulsed light beam 1011, which is provided to the lithography exposure apparatus 969. The photolithography system 1000 also includes a control system 1050, which, in the example of FIG. 10, is connected to components of the optical source 1005 as well as to the lithography exposure apparatus 969 to control various operations of the system 1000. In other implementations, the control system 1080 may be implemented as two separate control systems, one to control various aspects of the optical source 1005 and another to control the lithography exposure apparatus.

In the example shown in FIG. 10, the optical source 1005 is a two-stage laser system that includes a master oscillator (MO) 1001 that provides a seed light beam 1006 to a power amplifier (PA) 1002. The MO 1001 and the PA 1002 may be considered to be subsystems of the optical source 1005 or systems that are part of the optical source 1005. The power amplifier 1002 receives the seed light beam 1006 from the master oscillator 1001 and amplifies the seed light beam 1006 to generate the light beam 1011 for use in the lithography exposure apparatus 969. For example, the master oscillator 1001 may emit a pulsed seed light beam, with seed pulse energies of approximately 1 milliJoule (mJ) per pulse, and these seed pulses may be amplified by the power amplifier 1002 to about 10 to 15 mJ.

The master oscillator 1001 includes a discharge chamber 1010_1 having two elongated electrodes 1014a_1 and 1014b_1, a gain medium 1018_1 that is a gas mixture, and a fan (not shown) for circulating the gas mixture between the electrodes 1014a_1, 1014b_1. A resonator is formed between a line narrowing module 1086 on one side of the discharge chamber 1010_1 and an output coupler 1081 on a second side of the discharge chamber 1010_1. The line narrowing module 1086 may include a diffractive optic such as a grating that finely tunes the spectral output of the discharge chamber 1010_1. The optical source 1005 also includes a line center analysis module 1084 that receives an output light beam from the output coupler 1081 and a beam coupling optical system 1038. The line center analysis module 1084 is a measurement system that may be used to measure or monitor the wavelength of the seed light beam 1006. The line center analysis module 1084 may be placed at other locations in the optical source 1005, or it may be placed at the output of the optical source 1005.

The gas mixture 1018_1 may be any gas suitable for producing a light beam at the wavelength and bandwidth required for the application. For an excimer source, the gas mixture 1018_1 may contain a noble gas (rare gas) such as, for example, argon or krypton, a halogen, such as, for example, fluorine or chlorine and traces of xenon apart from a buffer gas, such as helium. Specific examples of the gas mixture include argon fluoride (ArF), which emits light at a wavelength of about 193 nm, krypton fluoride (KrF), which emits light at a wavelength of about 248 nm, or xenon chloride (XeCl), which emits light at a wavelength of about 351 nm. The excimer gain medium (the gas mixture) is pumped with short (for example, nanosecond) current pulses in a high-voltage electric discharge by application of a voltage to the elongated electrodes 1014a_1, 1014b_1.

The power amplifier 1002 includes a beam coupling optical system 1083 that receives the seed light beam 1006 from the master oscillator 1001 and directs the seed light beam 1006 through a discharge chamber 1010_2, and to a beam turning optical element 1082, which modifies or changes the direction of the seed light beam 1006 so that it is sent back into the discharge chamber 1010_2. The beam turning optical element and the beam coupling optical system 1083 form a circulating and closed loop path in which the input into a ring amplifier intersects the output of the ring amplifier at the beam coupling optical system 1083.

The discharge chamber 1010_2 includes a pair of elongated electrodes 1014a_2, 1014b_2, a gas mixture 1018_2, and a fan (not shown) for circulating the gas mixture 1018_2 between the electrodes 1014a_2, 1014b_2. The gas mixture 1018_2 may be the same as the gas mixture 1018_1. The gas mixture 1018_1 and/or the gas mixture 1018_2 may be interacted with a scrubber (such as the scrubber 215 of FIG. 2) and exhausted as the exhaust gas mixture 232 to the gas management system 200. The gas mixture 1018_1 and/or the gas mixture 1018_2 may include or be the recycled gas mixture 234 supplied by the gas management system 200.

The output light beam 1011 may be directed through a beam preparation system 1085 prior to reaching the lithography exposure apparatus 969. The beam preparation system 1085 may include a bandwidth analysis module that measures various parameters (such as the bandwidth or the wavelength) of the beam 1011. The beam preparation system 1085 also may include a pulse stretcher (not shown) that stretches each pulse of the output light beam 1011 in time. The beam preparation system 1085 also may include other components that are able to act upon the beam 1011 such as, for example, reflective and/or refractive optical elements (such as, for example, lenses and mirrors), filters, and optical apertures (including automated shutters).

The photolithography system 1000 also includes a control system 1080. The control system 1080 may control when the optical source 1005 emits a pulse of light or a burst of light pulses that includes one or more pulses of light by sending one or more signals to the optical source 1005. The control system 1080 is also connected to the lithography exposure apparatus 969. Thus, the control system 1080 also may control the various aspects of the lithography exposure apparatus 969. For example, the control system 1080 may control the exposure of the wafer 970 (FIG. 9B) and thus may be used to control how electronic features are printed on the wafer 970. In some implementations, the control system 1080 may control the scanning of the wafer 970 by controlling the motion of the slit 976 in the x-y plane (FIG. 9B). Moreover, the control system 1050 may exchange data with the metrology system 972 and/or the optical system 975 (FIG. 9B).

The lithography exposure apparatus 969 also may include, for example, temperature control devices (such as air conditioning devices and/or heating devices), and/or power supplies for the various electrical components. The control system 1080 also may control these components. In some implementations, the control system 1080 is implemented to include more than one sub-control system, with at least one sub-control system (a lithography controller) dedicated to controlling aspects of the lithography exposure apparatus 969. In these implementations, the control system 1080 may be used to control aspects of the lithography exposure apparatus 969 instead of, or in addition to, using the lithography controller.

When the gain medium of the gas mixture 1018_1 or the gas mixture 1018_2 is pumped by applying voltage to the electrodes 1014a_1, 1014b_1 or 1014a_2, 1014b_2, respectively, the gain medium of the gas mixture 1018_1 and/or 1018_2 emits light. When voltage is applied to the electrodes at regular temporal intervals, the light beam 1011 is pulsed. Thus, the repetition rate of the pulsed light beam 1011 is determined by the rate at which voltage is applied to the electrodes. The repetition rate of the pulses may range between about 500 and 6,000 Hz for most applications. In some implementations, the repetition rate may be greater than 6,000 Hz, and may be, for example, 12,000 Hz or greater.

The embodiments may further be described using the following clauses:

1. A gas chamber supply system comprising:
   a first gas source configured to fluidly connect to a first inlet of a first gas chamber and configured to supply a first gas mixture that contains a first plurality of gases, at least one of the gases in the first plurality includes a halogen;
   a second gas source configured to fluidly connect to a second inlet of the first gas chamber and configured to supply a second gas mixture that contains a second plurality of gases, the second plurality of gases lacking a halogen, the second gas source comprising:
   a pre-prepared gas supply including the second gas mixture;
   a recycled gas supply including the second gas mixture; and
   a fluid flow switch connected to the pre-prepared gas supply and to the recycled gas supply;
   a gas analysis system that receives a sample of the recycled gas supply and analyzes gas components within the recycled gas supply; and
   a control system connected to the gas analysis system and to the fluid flow switch and configured to:
   receive the analysis from the gas analysis system;
   determine if the relative concentration between the gas components within the recycled gas supply is within an acceptable range; and
   provide a signal to the fluid flow switch to thereby select one of the pre-prepared gas supply and the recycled gas supply as the second gas source based on the determination.

2. The gas chamber supply system of clause 1, further comprising a pressure measurement system that measures a pressure of the recycled gas supply, wherein the control system receives an output from the pressure measurement system, and adjusts the signal to the fluid flow switch based on the output from the pressure measurement system.

3. The gas chamber supply system of clause 1, wherein the second gas mixture includes at least a gain medium component having a noble gas and at least a buffer component.

4. The gas chamber supply system of clause 3, wherein the noble gas in the gain medium component is Ar and the buffer component includes a noble gas.

5. The gas chamber supply system of clause 3, wherein the analysis of the gas components within the recycled gas supply includes measuring an amount of the gain medium component having the noble gas and measuring an amount of the buffer component.

6. The gas chamber supply system of clause 1, wherein the recycled gas supply including the gas mixture is received from a gas blending system of a gas recycle system.

7. The gas chamber supply system of clause 1, wherein the gas analysis system comprises a mass spectrometer, a gas chromatograph, or a Fourier-transform infrared (FTIR) spectrometer.

8. A gas chamber supply system comprising:
   a first gas source configured to fluidly connect to a first inlet of a first gas chamber and configured to supply a first gas mixture that contains a first plurality of gases, at least one of the gases in the first plurality includes a halogen;
   a second gas source configured to fluidly connect to a second inlet of the first gas chamber and configured to supply a second gas mixture that contains a second plurality of gases, the second plurality of gases lacking a halogen, the second gas source comprising:
   a pre-prepared gas supply including the second gas mixture;
   a recycled gas supply including the second gas mixture; and
   a fluid flow switch connected to the pre-prepared gas supply and to the recycled gas supply; and
   a gas recycle system configured to supply the second gas mixture to the recycled gas supply, the gas recycle system comprising:
   a gas purifier system configured to receive a gas mixture exhausted from a second gas chamber that is distinct from the first gas chamber;
   a gas analysis system that receives the purified gas mixture and analyzes the gas components within the purified gas mixture; and
   a gas blending system that prepares a recycled gas mixture and outputs the recycled gas mixture as the second gas mixture of the recycled gas supply; and
   a control system connected to the gas recycle system and to the fluid flow switch, and configured to provide a signal to the fluid flow switch to thereby select one of the pre-prepared gas supply and the recycled gas supply as the second gas source.

9. The gas chamber supply system of clause 8, further comprising a pressure measurement system that measures a pressure of the recycled gas supply, wherein the control system receives an output from the pressure measurement system, and adjusts the signal to the fluid flow switch based on the output from the pressure measurement system.

10. The gas chamber supply system of clause 8, wherein the purified gas mixture includes at least a gain medium component having a noble gas and at least a buffer component.

11. The gas chamber supply system of clause 10, wherein the noble gas in the gain medium component is Ar and the buffer component includes a noble gas.

12. The gas chamber supply system of clause 10, wherein the analysis of the gas components within the purified gas mixture includes measuring an amount of the gain medium component having the noble gas and measuring an amount of the buffer component.

13. The gas chamber supply system of clause 8, wherein the gas analysis system comprises a mass spectrometer, a gas chromatograph, or a Fourier-transform infrared (FTIR) spectrometer.

14. A gas chamber supply system comprising:
  a first gas source configured to fluidly connect to a first inlet of a first set of gas chambers, and configured to supply a first gas mixture that contains a first plurality of gases, at least one of the gases in the first plurality includes a halogen;
  a second gas source configured to fluidly connect to a second inlet of the first set of gas chambers, and configured to supply a second gas mixture that contains a second plurality of gases, the second plurality of gases lacking a halogen, the second gas source comprising:
  a pre-prepared gas supply including the second gas mixture;
  a recycled gas supply including the second gas mixture; and
  a fluid flow switch connected to the pre-prepared gas supply and to the recycled gas supply; and
  a gas recycle system configured to supply the second gas mixture to the recycled gas supply, the gas recycle system comprising:
  a gas purifier system fluidly connected to the output to receive a gas mixture exhausted from at least one of the gas chambers of a second set of gas chambers;
  a gas analysis system that receives the purified gas mixture and analyzes the gas components within the purified gas mixture; and
  a gas blending system that prepares a recycled gas mixture and outputs the recycled gas mixture as the second gas mixture of the recycled gas supply; and
  a control system connected to the gas recycle system and to the fluid flow switch, and configured to provide a signal to the fluid flow switch to thereby select one of the pre-prepared gas supply and the recycled gas supply as the second gas source.

15. The gas chamber supply system of clause 14, wherein one or more of the gas chambers of the second set correspond to one or more of the gas chambers of the first set.

16. The gas chamber supply system of clause 14, further comprising a pressure measurement system that measures a pressure of the recycled gas supply, wherein the control system receives an output from the pressure measurement system, and adjusts the signal to the fluid flow switch based on the output from the pressure measurement system.

17. The gas chamber supply system of clause 14, wherein the second gas mixture includes at least a gain medium component having a noble gas and at least a buffer component.

18. The gas chamber supply system of clause 17, wherein the noble gas in the gain medium component is Ar and the buffer component includes a noble gas.

19. The gas chamber supply system of clause 17, wherein the analysis of the gas components within the recycled gas supply includes measuring an amount of the gain medium component having the noble gas and measuring an amount of the buffer component.

20. The gas chamber supply system of clause 14, wherein the gas analysis system comprises a mass spectrometer, a gas chromatograph, or a Fourier-transform infrared (FTIR) spectrometer.

Other implementations are within the scope of the claims.

What is claimed is:

1. A gas chamber supply system comprising:
  a first gas source configured to fluidly connect to a first inlet of a first gas chamber and configured to supply a first gas mixture that contains a first plurality of gases, at least one of the gases in the first plurality includes a halogen;
  a second gas source configured to fluidly connect to a second inlet of the first gas chamber and configured to supply a second gas mixture that contains a second plurality of gases, the second plurality of gases lacking a halogen, the second gas source comprising:
  a pre-prepared gas supply including the second gas mixture;
  a recycled gas supply including the second gas mixture; and
  a fluid flow switch connected to the pre-prepared gas supply and to the recycled gas supply;
  a gas analysis system that receives a sample of the recycled gas supply and analyzes gas components within the recycled gas supply; and
  a control system connected to the gas analysis system and to the fluid flow switch and configured to:
  receive the analysis from the gas analysis system;
  determine if the relative concentration between the gas components within the recycled gas supply is within an acceptable range; and
  provide a signal to the fluid flow switch to thereby select one of the pre-prepared gas supply and the recycled gas supply as the second gas source based on the determination.

2. The gas chamber supply system of claim 1, further comprising a pressure measurement system that measures a pressure of the recycled gas supply, wherein the control system receives an output from the pressure measurement system, and adjusts the signal to the fluid flow switch based on the output from the pressure measurement system.

3. The gas chamber supply system of claim 1, wherein the second gas mixture includes at least a gain medium component having a noble gas and at least a buffer component.

4. The gas chamber supply system of claim 3, wherein the noble gas in the gain medium component is argon (Ar) and the buffer component includes a noble gas.

5. The gas chamber supply system of claim 3, wherein the analysis of the gas components within the recycled gas supply includes measuring an amount of the gain medium component having the noble gas and measuring an amount of the buffer component.

6. The gas chamber supply system of claim 1, wherein the recycled gas supply including the gas mixture is received from a gas blending system of a gas recycle system.

7. The gas chamber supply system of claim 1, wherein the gas analysis system comprises a mass spectrometer, a gas chromatograph, or a Fourier-transform infrared (FTIR) spectrometer.

8. The gas chamber supply system of claim 1, further comprising a fluid conduit configured to fluidly connect the first gas source to the first fluid inlet, and a fluid bus configured to fluidly connect the second gas source to the second fluid inlet.

9. A gas chamber supply system comprising:
a first gas source configured to fluidly connect to a first inlet of a first gas chamber and configured to supply a first gas mixture that contains a first plurality of gases, at least one of the gases in the first plurality includes a halogen;
a second gas source configured to fluidly connect to a second inlet of the first gas chamber and configured to supply a second gas mixture that contains a second plurality of gases, the second plurality of gases lacking a halogen, the second gas source comprising:
a pre-prepared gas supply including the second gas mixture;
a recycled gas supply including the second gas mixture; and
a fluid flow switch connected to the pre-prepared gas supply and to the recycled gas supply; and
a gas recycle system configured to supply the second gas mixture to the recycled gas supply, the gas recycle system comprising:
a gas purifier system configured to receive a gas mixture exhausted from a second gas chamber that is distinct from the first gas chamber;
a gas analysis system that receives the purified gas mixture and analyzes the gas components within the purified gas mixture; and
a gas blending system that prepares a recycled gas mixture and outputs the recycled gas mixture as the second gas mixture of the recycled gas supply; and
a control system connected to the gas recycle system and to the fluid flow switch, and configured to provide a signal to the fluid flow switch to thereby select one of the pre-prepared gas supply and the recycled gas supply as the second gas source.

10. The gas chamber supply system of claim 9, further comprising a pressure measurement system that measures a pressure of the recycled gas supply, wherein the control system receives an output from the pressure measurement system, and adjusts the signal to the fluid flow switch based on the output from the pressure measurement system.

11. The gas chamber supply system of claim 9, wherein the purified gas mixture includes at least a gain medium component having a noble gas and at least a buffer component.

12. The gas chamber supply system of claim 11, wherein the noble gas in the gain medium component is argon (Ar) and the buffer component includes a noble gas.

13. The gas chamber supply system of claim 11, wherein the analysis of the gas components within the purified gas mixture includes measuring an amount of the gain medium component having the noble gas and measuring an amount of the buffer component.

14. The gas chamber supply system of claim 9, wherein the gas analysis system comprises a mass spectrometer, a gas chromatograph, or a Fourier-transform infrared (FTIR) spectrometer.

15. A gas chamber supply system comprising:
a first gas source configured to fluidly connect to a first inlet of a first set of gas chambers, and configured to supply a first gas mixture that contains a first plurality of gases, at least one of the gases in the first plurality includes a halogen;
a second gas source configured to fluidly connect to a second inlet of the first set of gas chambers, and configured to supply a second gas mixture that contains a second plurality of gases, the second plurality of gases lacking a halogen, the second gas source comprising:
a pre-prepared gas supply including the second gas mixture;
a recycled gas supply including the second gas mixture; and
a fluid flow switch connected to the pre-prepared gas supply and to the recycled gas supply; and
a gas recycle system configured to supply the second gas mixture to the recycled gas supply, the gas recycle system comprising:
a gas purifier system fluidly connected to the output to receive a gas mixture exhausted from at least one of the gas chambers of a second set of gas chambers;
a gas analysis system that receives the purified gas mixture and analyzes the gas components within the purified gas mixture; and
a gas blending system that prepares a recycled gas mixture and outputs the recycled gas mixture as the second gas mixture of the recycled gas supply; and
a control system connected to the gas recycle system and to the fluid flow switch, and configured to provide a signal to the fluid flow switch to thereby select one of the pre-prepared gas supply and the recycled gas supply as the second gas source.

16. The gas chamber supply system of claim 15, further comprising a pressure measurement system that measures a pressure of the recycled gas supply, wherein the control system receives an output from the pressure measurement system, and adjusts the signal to the fluid flow switch based on the output from the pressure measurement system.

17. The gas chamber supply system of claim 15, wherein the second gas mixture includes at least a gain medium component having a noble gas and at least a buffer component.

18. The gas chamber supply system of claim 17, wherein the noble gas in the gain medium component is argon (Ar) and the buffer component includes a noble gas.

19. The gas chamber supply system of claim 17, wherein the analysis of the gas components within the recycled gas supply includes measuring an amount of the gain medium component having the noble gas and measuring an amount of the buffer component.

20. The gas chamber supply system of claim 15, wherein the gas analysis system comprises a mass spectrometer, a gas chromatograph, or a Fourier-transform infrared (FTIR) spectrometer.

* * * * *